United States Patent
Kang et al.

(10) Patent No.: US 10,370,391 B2
(45) Date of Patent: Aug. 6, 2019

(54) HYDROGEN PEROXIDE-ACTIVABLE, ANTI-OXIDANT COMPOUNDS AND METHODS USING SAME

(71) Applicants: Beth Israel Deaconess Medical Center, Inc., Boston, MA (US); Chonbuk National University Industrial Cooperation Foundation, Jeonju, Jeonbuk (KR)

(72) Inventors: Peter M. Kang, Boston, MA (US); Dongwon Lee, Jeonbuk (KR); Seunggyu Park, Jeonbuk (KR); Dahee Jeong, Jeonbuk (KR)

(73) Assignees: Beth Israel Deaconess Medical Center, Inc., Boston, MA (US); Chonbuk National University Industrial Cooperation Foundation, Jeonju (KR)

( * ) Notice: Subject to any disclaimer, the term of this patent is extended or adjusted under 35 U.S.C. 154(b) by 0 days.

(21) Appl. No.: 15/583,517

(22) Filed: May 1, 2017

(65) Prior Publication Data
US 2018/0105540 A1    Apr. 19, 2018

Related U.S. Application Data

(63) Continuation-in-part of application No. PCT/US2015/058619, filed on Nov. 2, 2015.
(Continued)

(51) Int. Cl.
*A61P 29/00* (2006.01)
*C07F 5/02* (2006.01)
(Continued)

(52) U.S. Cl.
CPC ............ *C07F 5/025* (2013.01); *A61K 9/5031* (2013.01); *A61K 31/69* (2013.01); *A61P 29/00* (2018.01)

(58) Field of Classification Search
CPC .......... A61P 29/00; C07F 5/025; A62K 31/69
See application file for complete search history.

(56) References Cited

U.S. PATENT DOCUMENTS

| | | | |
|---|---|---|---|
| 2006/0009805 A1 | 1/2006 | Jensen et al. | |
| 2014/0255311 A1* | 9/2014 | Almutairi | A61K 47/34 424/9.3 |
| 2017/0014518 A1 | 1/2017 | Lee et al. | |

FOREIGN PATENT DOCUMENTS

| JP | 2000098557 A | 4/2000 |
|---|---|---|
| WO | 2013147795 A1 | 10/2013 |

OTHER PUBLICATIONS

Brackman et al, ("Synthesis and Evaluation Thiazolidinedione and Dioxazaborocane Analogues as Inhibitors of Al-2 Quorum Sensing in Vibrio Harveyi", Bioorganic & Medicinal Chemistry, Pergamon, GB, vol. 21, No. 3, Dec. 11, 2012 (Dec. 11, 2012), pp. 660-667).*
(Continued)

*Primary Examiner* — Carlos A Azpuru
(74) *Attorney, Agent, or Firm* — Melissa Hunter-Ensor; Wade Haaland; Greenberg Traurig, LLP

(57) ABSTRACT

The present invention includes 4-(hydroxymethyl)phenylboronic esters, which react with hydrogen peroxide to form 4-hydroxybenzyl alcohol, which is an anti-inflammatory and/or anti-oxidant compound, as well as microparticles and compositions thereof. In certain embodiments, the compositions of the invention may be used to treat or prevent oxidative stress and/or inflammation, including ischemic disease.

8 Claims, 28 Drawing Sheets

Related U.S. Application Data

(60) Provisional application No. 62/074,195, filed on Nov. 3, 2014.

(51) Int. Cl.
*A61K 9/50* (2006.01)
*A61K 31/69* (2006.01)

(56) References Cited

OTHER PUBLICATIONS

International Search Report and Written Opinion for corresponding PCT/US2015/058619, dated Jan. 12, 2016 (16 pages).
Brackman, G. et al., "Synthesis and evaluation of thiazolidinedione and dioxazaborocane analogues as inhibitors of AI-2 quorum sensing inVibrio harveyi," Bioorganic & Medicinal Chemistry, Pergamon, GB, vol. 21, No. 3, Dec. 11, 2012, pp. 660-667.
Lee-Chiang, L. et al., "Development of highly selective and sensitive probes for hydrogen peroxideElectronic supplementary information (ESI) available: general methods., see http://www.rsc.org/suppdata/cc/b3/b309393j/", Chemical Communications—Chemcom, No. 21, Jan. 1, 2003, p. 2728.
Chen, W. et al., "Aromatic Nitrogen Mustard-Based Prodrugs: Activity Selectivity, and the Mechanism of DNA Cross-Linking," Chemistry—A European Journal, vol. 20, No. 24, May 7, 2014, pp. 7410-7418.
Ikeda, M. et al, "Rational Molecular Design of Stimulus-Responsive Supramolectular Hydrogels Based on Dipeptides," Advanced Materials, vol. 23, No. 25, Apr. 29, 2011, pp. 2819-2822.

\* cited by examiner

HYDROGEN PEROXIDE-ACTIVABLE, ANTI-OXIDANT COMPOUNDS AND METHODS USING SAME

CROSS-REFERENCE TO RELATED APPLICATIONS

This application is a continuation-in-part of PCT International Application No. PCT/US2015/058619, filed Nov. 2, 2015, designating the United States and published in English, which claims priority to and benefit of U.S. Provisional Patent Application Ser. No. 62/074,195, filed Nov. 3, 2014. The entire contents of these applications are hereby incorporated by reference herein.

STATEMENT OF RIGHTS TO INVENTIONS MADE UNDER FEDERALLY SPONSORED RESEARCH

This invention was made with government support under Grant No. HL091998 awarded by the National Institutes of Health. The government has certain rights in the invention.

BACKGROUND OF THE INVENTION

Hydrogen peroxide ($H_2O_2$) is an essential oxygen metabolite and serves as a messenger in cellular signal pathways that are necessary for the growth, development and fitness of living organisms. $H_2O_2$ is one of reactive oxygen species (ROS) and is also a precursor of highly toxic ROS such as hydroxyl radical, peroxinitrite and hypochloride. A large body of evidence indicates that accumulation of $H_2O_2$ causes oxidative stress and inflammation events, which are highly correlated with the onset and development of various pathological conditions such as cancer, diabetic, cardiovascular diseases and ischemia-reperfusion (I/R) injury. I/R injuries are seen in a variety of clinical conditions, such as acute coronary syndrome, hepatic and renal ischemic insults, cardiopulmonary bypass surgery and vascular thromboembolic events. Reperfusion of blood flow in ischemic tissues induces a large generation of $H_2O_2$ which is the most abundant form of the ROS in I/R injury and causes oxidative stress and cellular damages, further exacerbating tissue damages. Thus, $H_2O_2$ is an attractive target of oxidative stress-associated diseases and targeted therapy directed to the site of I/R injury, which is characterized by high concentration of $H_2O_2$ production, will offer significant advantages over a generalized, antioxidant therapy.

4-Hydroxybenzyl alcohol (HBA) is one of major active components of *Gastrodia elata*, a widely used herbal agent for the treatment of inflammatory diseases and convulsive disorders in Asia. HBA exerts anti-oxidant activities and plays a protective role against oxidative stress-related diseases such as coronary heart diseases and ischemic brain injury. HBA is also a powerful scavenger of hydroxyl radical and superoxide due to its phenolic hydroxyl group. There has been interest in the use of HBA as an anti-oxidant and therapeutic agent, but HBA is unable to scavenge $H_2O_2$ and has a short blood circulation time, limiting its clinical applications.

There is a need in the art to develop novel compounds that are useful in treating or preventing oxidative stress injury in a subject. Such compounds would be useful in treating or preventing ROS-derived oxidative stress and/or inflammation in the subject.

SUMMARY OF THE INVENTION

As described below, the present invention generally features anti-oxidant boronic esters capable of activation by hydrogen peroxide, compositions containing these compounds, and methods of using these compositions as anti-oxidative agents, for example, for the treatment of ischemic/reperfusion injury.

The present invention provides a 4-(hydroxymethyl)phenylboronic ester.

The present invention further provides a microparticle comprising any of the boronic esters of the invention.

The present invention further provides a pharmaceutical composition comprising any of the boronic esters of the invention and/or any of the microparticles of the invention.

The present invention further provides a drug delivery system comprising any of the esters of the invention, any of the microparticles of the invention, and/or any of the compositions of the invention.

The present invention further provides a method of treating or preventing oxidative stress injury in a subject in need thereof, wherein the method comprises administering to the subject a therapeutically effective amount of any of the esters of the invention, any of the microparticles of the invention, and/or any of the compositions of the invention, wherein the boronic ester undergoes at least partial degradation to release 4-hydroxybenzyl alcohol (HBA) within the body of the subject, thereby treating or preventing oxidative stress injury.

The present invention further provides a method of inhibiting or preventing the formation of reactive oxygen species (ROS) in at least one bodily site of a subject, wherein the method comprises administering to the subject a therapeutically effective amount of any of the esters of the invention, any of the microparticles of the invention, and/or any of the compositions of the invention, wherein the boronic ester undergoes at least partial degradation to release HBA within the body of the subject, and, whereby the formation of ROS in at least one bodily site of the subject is inhibited or prevented.

The present invention further provides a method for reducing ischemic damage or reperfusion injury in a tissue or organ for transplantation, the method comprising contacting the tissue or organ with any of the esters of the invention, any of the microparticles of the invention, and/or any of the compositions of the invention, before, during or after transplantation, thereby reducing ischemic damage or reperfusion injury in the tissue or organ relative to a reference.

The present invention further provides a method of reducing apoptosis associated with ischemic reperfusion injury in a subject, the method comprising administering to the subject an effective amount of any of the esters of the invention, any of the microparticles of the invention, and/or any of the compositions of the invention, thereby reducing apoptosis associated with ischemic reperfusion injury relative to a reference.

The present invention further provides a method of reducing inflammation associated with ischemic reperfusion injury in a subject, the method comprising administering to the subject an effective amount of any of the esters of the invention, any of the microparticles of the invention, and/or any of the compositions of the invention, thereby reducing inflammation associated with ischemic reperfusion injury relative to a reference.

In certain embodiments, the ester further comprises an alcohol selected from the group consisting of a diol, triol, tetraol, pentaol, hexaol and a higher polyol, wherein the alcohol and 4-(hydroxymethyl)phenylboronic acid are covalently conjugated to form the boronic ester. In other embodiments, the alcohol comprises a diol or a triol. In yet other embodiments, the alcohol comprises 1,3-propanediol or 2-(hydroxymethyl)-2-methylpropane-1,3-diol. In yet other embodiments, the boronic ester comprises 4-(5-(hydroxymethyl)-5-methyl-1,3,2-dioxaborinan-2-yl)phenyl methanol or 4-(1,3,2-dioxaborinan-2-yl)phenyl methanol.

In certain embodiments, the microparticle is biocompatible and biodegradable. In other embodiments, the microparticle comprises a polymer or liposome. In yet other embodiments, the polymer comprises at least one selected from the group consisting of poly(lactic acid) (PLA), poly(glycolic acid) (PGA), poly(lactic-co-glycolic acid) (PLGA), and poly (ε-caprolactone) (PCL).

In certain embodiments, the oxidative stress injury is ischemic/reperfusion injury associated with acute coronary syndrome, hepatic ischemia, renal ischemia, brain ischemia, coronary artery disease, cardiopulmonary bypass surgery, whole body ischemia/reperfusion, and/or a vascular thromboembolic event. In other embodiments, the method reduces apoptosis or inflammation associated with ischemic/reperfusion injury. In yet other embodiments, the ROS comprises a superoxide or peroxide species. In yet other embodiments, the tissue or organ is a cardiac tissue, heart, kidney tissue, kidney, hepatic tissue, liver, lung tissue, lung, pancreatic tissue, pancreas, intestine tissue, intestine, thymus, bone, cartilage, muscular tissue, tendon, cornea, epithelial tissue, skin, cardiac valve, neurons, nerves, endothelial tissue, artery, or vein.

In certain embodiments, the subject is a mammal. In other embodiments, the tissue or organ is from a mammal. In yet other embodiments, the mammal is human.

In certain embodiments, the method reduces cardiac, hepatic or neuronal apoptosis. In other embodiments, the method reduces cardiac dysfunction as assessed by PV loop analysis and/or echocardiography. In yet other embodiments, the reference is the level of apoptosis present in an untreated control subject. In yet other embodiments, the method reduces TNF-α and/or inducible nitric oxide synthase levels in the subject. In yet other embodiments, the reference is the level of inflammation present in an untreated control subject. In yet other embodiments, the apoptosis or inflammation is associated with acute coronary syndrome, hepatic ischemia, renal ischemia, brain ischemic injury, coronary artery disease, cardiopulmonary bypass surgery and/or a vascular thromboembolic event.

In certain embodiments, the invention provides 4-(hydroxymethyl)phenylboronic esters and methods of using such compounds as anti-oxidants. Compositions and articles defined by the invention were isolated or otherwise manufactured in connection with the examples provided below. Other features and advantages of the invention will be apparent from the detailed description, and from the claims.

Definitions

Unless defined otherwise, all technical and scientific terms used herein generally have the same meaning as commonly understood by one of ordinary skill in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5$^{th}$ Ed., R. Rieger et al. (eds.), Springer Verlag (1991); and Hale & Marham, The Harper Collins Dictionary of Biology (1991). Generally, the nomenclature used herein and the laboratory procedures in medicine, organic chemistry and polymer chemistry are those well-known and commonly employed in the art.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "administration" means providing the composition of the present invention to a subject by any suitable method.

As used herein, the term "BRAP" refers to (4-(5-(hydroxymethyl)-5-methyl-1,3,2-dioxaborinan-2-yl)phenyl) methanol.

As used herein, the term "CPB" surgery refers to cardiopulmonary bypass surgery.

As used herein, the term "CABG" surgery refers to coronary arterial bypass graft surgery.

As used herein, the term "composition" or "pharmaceutical composition" refers to a mixture of at least one compound useful within the invention with a pharmaceutically acceptable carrier. The pharmaceutical composition facilitates administration of the compound to a subject.

As used herein, the term "DCF" refers to dichlorodihydrofluorescein.

As used herein, the term "DCFH-DA" refers to dichlorofluorescin-diacetate.

By "disease" is meant any condition or disorder that damages or interferes with the normal function of a cell, tissue, or organ. Examples of diseases include ischemic diseases, such as brain ischemia, heart ischemia, retinal ischemia, ischemic colitis, critical limb ischemia, ischemic acute renal failure, stroke, brain trauma, fetal hypoxia, ischemia/reperfusion injury or ischemia/reperfusion injury complications. Ischemia/reperfusion injury may be associated with cardiopulmonary bypass (CPB) surgery, wherein CPB surgery includes coronary arterial bypass graft (CABG) surgery; valve, defect or aneurysm repair; heart and/or lung transplantation; pulmonary thrombectomy; or pulmonary thromboendarterectomy, as well as ischemia/ reperfusion injury complications associated with CPB (and/ or CABG) surgery, such as atrial fibrillation, infarct extension, with reocclusion of an infarct-related artery (IRA), recurrent infarction, arrhythmia, stroke, small-to-moderate myocardial infarction, ventricular tachycardia/fibrillation, and congestive heart failure. Compounds of the invention are also useful for reducing ischemic injury of transplanted tissues, including solid organ transplantation (such as liver, kidney, lung or heart) or for solid organ preservation (such as liver, kidney, lung or heart). In particular embodiments, methods of the invention are useful for ischemic/reperfusion injury associated with acute coronary syndrome, hepatic ischemia, renal ischemia, brain ischemic injury, coronary artery disease, cardiopulmonary bypass surgery and/or a vascular thromboembolic event.

As used herein, the term "DMSO" refers to dimethyl sulfoxide.

As used herein, the term "DOX" refers to doxorubicin or a salt thereof.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

As used herein, the term "HBA" refers to 4-hydroxybenzyl alcohol, or a salt or solvate thereof.

As used herein, the term "iNOS" refers to inducible nitric oxide synthase.

As used herein, the term "instructional material" includes a publication, a recording, a diagram, or any other medium of expression that may be used to communicate the usefulness of the compositions of the invention. In some instances, the instructional material may be part of a kit useful for administering a compound or composition of the invention. The instructional material of the kit may, for example, be affixed to a container that contains the compounds and/or compositions of the invention or be shipped together with a container that contains the compositions. Alternatively, the instructional material may be shipped separately from the container with the intention that the recipient uses the instructional material and the compositions cooperatively. For example, the instructional material is for use of a kit; instructions for use of the compositions; or instructions for use of a formulation of the compositions.

As used herein, the term "I/R" refers to ischemic/reperfusion.

As used herein, the term "LPS" refers to lipopolysaccharide.

As used herein, the term "MCP-1" refers to monocyte chemotactic protein-1.

As used herein, the term "microparticle" refers to a particle with an average diameter ranging from about 10 nm to 1,000 µm. In one embodiment, the average diameter of the particle ranges from about 100 nm to 100 µm. In another embodiment, the average diameter of the particle ranges from about 100 nm to 10 µm. In yet another embodiment, the average diameter of the particle ranges from about 200 nm to 1 µm. In yet another embodiment, the average diameter of the particle ranges from about 200 nm to 800 nm. In yet another embodiment, the average diameter of the particle is about 500 nm. In yet another embodiment, the particle is approximately spherical.

As used herein, the term "MTT" refers to 3-(4,5-dimethylthiazol-2-yl)-2,5-diphenyl tetrazolium bromide.

As used herein, the term "OVA" refers to ovalbumin.

By "oxidative stress injury" is meant cell damage associated with a reactive oxygen species.

As used herein, the term "PCL" refers to poly(ε-caprolactone) or a salt thereof.

As used herein, the term "PGA" refers to poly(glycolic acid) or a salt thereof.

As used herein, the term "pharmaceutically acceptable" refers to a material, such as a carrier or diluent, which does not abrogate the biological activity or properties of the compound useful within the invention, and is relatively non-toxic, i.e., the material may be administered to a subject without causing undesirable biological effects or interacting in a deleterious manner with any of the components of the composition in which it is contained.

As used herein, the term "PLA" refers to poly(lactic acid) or a salt thereof.

As used herein, the term "PLGA" refers to poly(lactic-co-glycolic acid) or a salt thereof.

The term "prevent," "preventing" or "prevention," as used herein, means avoiding or delaying the onset of symptoms associated with a disease or condition in a subject that has not developed such symptoms at the time the administering of an agent or compound commences. Disease, condition and disorder are used interchangeably herein.

By "reference" is meant a standard or control condition.

As used herein, the term "ROS" refers to reactive oxygen species. ROS are chemically reactive molecules containing oxygen, and include oxygen ions, superoxides and peroxides.

As used herein, the term "reaction condition" refers to a physical treatment, chemical reagent, or combination thereof, which is required or optionally required to promote a reaction. Non-limiting examples of reaction conditions are electromagnetic radiation, heat, a catalyst, a chemical reagent (such as, but not limited to, an acid, base, electrophile or nucleophile), and a buffer.

As used herein, the term "salt" refers to a salt of a compound contemplated within the invention, including inorganic acids, organic acids, inorganic bases, organic bases, solvates, hydrates, or clathrates thereof. As used herein, the term "salt" embraces addition salts of free acids or free bases that are compounds useful within the invention. Suitable acid addition salts may be prepared from an inorganic acid or an organic acid. Examples of inorganic acids include hydrochloric, hydrobromic, hydriodic, nitric, carbonic, sulfuric, phosphoric, perchloric and tetrafluoroboronic acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Suitable base addition salts of compounds useful within the invention include, for example, metallic salts including alkali metal, alkaline earth metal and transition metal salts such as, for example, lithium, calcium, magnesium, potassium, ammonium, sodium and zinc salts. Acceptable base addition salts also include organic salts made from basic amines such as, for example, N,N'-dibenzyl ethylenediamine, chloroprocaine, choline, diethanolamine, ethylenediamine, meglumine (N-methyl-glucamine) and procaine. All of these salts may be prepared by conventional means from the corresponding free base compound by reacting, for example, the appropriate acid or base with the corresponding free base.

As used herein, the term "subject," "patient" or "individual" may be a human or non-human mammal or a bird. Non-human mammals include, for example, livestock and pets, such as ovine, bovine, equine, porcine, canine, feline and murine mammals. Preferably, the subject is human.

As used herein, the term "THF" refers to tetrahydrofuran.

As used herein, the term "TNF-α" refers to tumor necrosis factor-alpha.

The terms "treat" and "treating" and "treatment" as used herein refer to reducing the frequency or severity with which symptoms of a disease or condition are experienced by a subject by virtue of administering an agent or compound to the subject.

As used herein, the term "TUNEL" refers to terminal deoxynucleotidyl transferase dUTP nick end labeling.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments that are presently preferred. It should be understood, however, that the invention is not limited to the precise arrangements and instrumentalities of the embodiments shown in the drawings.

FIG. 1, comprising FIG. 1A: Exemplary synthetic route and degradation of BRAP as a $H_2O_2$-activable anti-oxidant prodrug. FIG. 1B: $^1H$ NMR spectra of BRAP before and after $H_2O_2$-mediated hydrolysis.

FIG. 2, comprising FIG. 2A: Exemplary change of UV-absorbance of BRAP in the presence of $H_2O_2$. FIG. 2B: $H_2O_2$ scavenging by various concentrations of BRAP. $H_2O_2$ solution (10 µM) was mixed with HBA or BRAP for 1 min, and the chemiluminescent intensity was measured by adding diphenyl oxalate (10 mg) and rubrene (1 mg). *$p<0.01$, **$p<0.001$ relative to $H_2O_2$ only group (n=4/group). FIG. 2C: $^1H$ NMR spectrum of BRAP under acidic condition (pH=3.0) after 72 h.

FIG. 3, comprising

FIG. 4, comprising FIGS. 4A-4B: Inhibitory effects on ROS generation in mouse macrophage cells stimulated by LPS (1 µg/mL) (FIG. 4A) or $H_2O_2$ (250 µM) (FIG. 4B). The generation of ROS was monitored by flow cytometry as an indicator of DCF fluorescence. Fluorescence was analyzed in 10,000 cells with excitation at 480 nm and emission at 530 nm. FIG. 4C: Protective effect of BRAP on $H_2O_2$—stimulated adult rat cardiomyocytes. V=vehicle, *<0.05 vs. V+$H_2O_2$ (n=4). FIG. 4D: Inhibitory effects on nitric oxide (NO) generation in LPS-stimulated cells. *$p<0.01$, $p<0.001$ relative to the LPS-treated group. (n=4/group). FIGS. 4E-4F: Inhibitory effects of BRAP on the generation TNF-α (FIG. 4E) and iNOS (FIG. 4F) in mouse macrophage cells stimulated with LPS. $p<0.001$ relative to the LPS treated group (n=4/group).

FIG. 5, comprising FIG. 5A: Hematoxylin and eosin (H/E) staining, DHE staining, and TUNEL staining of mouse liver after injection with HBA or BRAP. FIGS. 5B-5D: Quantitative analysis of serum ALT levels (FIG. 5B), cleaved caspase-3 protein expression (FIG. 5C), and TNF-α protein expression (FIG. 5D) after I/R injury. *$p<0.01$ relative to Veh I/R. †$p<0.05$ relative to HBA I/R (n=3~4/group). Actin protein expression was used as an internal control for protein loading.

FIG. 6, comprising FIG. 6A: Cardiac Output (CO) after BRAP administration for 2 weeks after I/R injury. *$p<0.05$ versus sham of each group, †$p<0.05$ versus Veh I/R (n=4~6/group). FIG. 6B: Representative confocal microscopy images of DHE staining of cardiomyocytes (DAPI: blue, DHE/DAPI: pink). FIG. 6C: Representative images of mRNA expression of inflammatory markers (TNF-α and MCP-1). 18S mRNA expression was used as an internal control. FIG. 6D: Caspase-3 activity assay after BRAP administration after I/R injury. *$p<0.05$ versus sham of each group, †$p<0.05$ versus Veh I/R (n=4~6/group). FIG. 6E: Representative confocal microscopy images of TUNEL staining of cardiomyocytes. FIG. 6F: Quantification of TUNEL positive cardiomyocytes/total cells. *$p<0.05$ versus sham of each group, †$p<0.05$ versus Veh I/R (n=3~4/group). DHE staining, mRNA expression measurement, caspase activity assay, and TUNEL analysis were done in heart tissue 24 hour after cardiac I/R injury.

FIG. 7, comprising FIGS. 7A-7B: Creatinine (FIG. 7A) and ALT (FIG. 7B) levels 7 days after daily BRAP administration. FIG. 7C: Representative H/E stained tissue sections of different organs 7 days after daily BRAP administration (n=4/group).

FIG. 8, comprising

FIG. 10, comprising

FIG. 11, comprising

FIG. 18, comprising FIG. 18A depicts a scanning electron micrograph (SEM) image of BRAP-encapsulated PLGA microparticles. FIG. 18B shows a graph of dynamic light scattering (x axis: diameter (nm); y axis: % light intensity) of BRAP-encapsulated PLGA microparticles suspended in PBS at pH 7.4. The microparticles were prepared using a conventional double emulsion method using poly (vinyl alcohol) as emulsifier.

FIG. 20, comprising FIG. 20A shows the control; FIG. 20B shows $H_2O_2$-stimulated cells; FIG. 20C shows cells treated with both $H_2O_2$ and PLGA; FIG. 20D shows $H_2O_2$-stimulated cells treated with BRAP-encapsulated PLGA microparticles containing 5% BRAP (PB5%), by weight; FIG. 20E shows $H_2O_2$-stimulated cells treated with BRAP-encapsulated PLGA microparticles containing 10% BRAP (PB10%), by weight. The antioxidant effects of the BRAP-encapsulated PLGA microparticles on the $H_2O_2$-stimulated RAW264.7 cells can be visualized.

DETAILED DESCRIPTION OF THE INVENTION

The present invention relates to the unexpected discovery of novel boronic esters, such as 4-(hydroxymethyl)phenylboronic esters. In certain embodiments, the boronic esters of the invention comprise (4-(5-(hydroxymethyl)-5-methyl-1, 3,2-dioxaborinan-2-yl)phenyl)methanol (BRAP). In other embodiments, the boronic esters of the invention react with $H_2O_2$ to form 4-hydroxybenzyl alcohol (HBA). The present invention further provides compositions comprising the boronic esters of the invention. In certain embodiments, the compounds and/or compositions of the invention are useful to treat and/or prevent oxidative-related diseases, including ischemic/reperfusion injury associated with acute coronary syndrome, hepatic ischemia, renal ischemia, brain ischemic injury, coronary artery disease, cardiopulmonary bypass surgery and/or a vascular thromboembolic event.

Overproduction of hydrogen peroxide ($H_2O_2$) causes oxidative stress and is the main culprit in the pathogenesis of ischemia/reperfusion (I/R) injury. Suppression of $H_2O_2$-induced oxidative stress is therefore critical in the treatment of I/R injury. The compounds of the invention are antioxidant prodrug activated by $H_2O_2$, and are capable of specifically targeting the site of oxidative stress and exerting anti-inflammatory and anti-apoptotic activities.

Figure 1A:
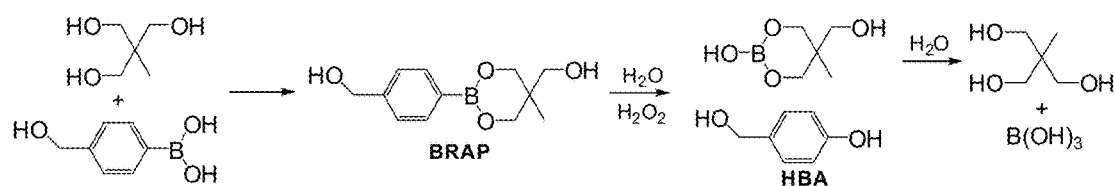
FIGS. 1A-1B, illustrates generation of $H_2O_2$ scavenging anti-oxidant BRAP.

As described herein, the invention provides phenylboronic esters that can be specifically cleaved by $H_2O_2$ to generate bioactive phenols. The boronic esters of the invention have excellent specific reactivity to $H_2O_2$ and are nontoxic. As illustrated in FIG. 1A, BRAP, which is the $H_2O_2$-activable, anti-oxidant boronated prodrug of HBA, was synthesized. Without wishing to be limited by any theory, a boronic ester compound such as BRAP affords at least two beneficial therapeutic actions. In one aspect, BRAP is rapidly and specifically oxidized by high levels of $H_2O_2$, subsequently limiting $H_2O_2$-mediated oxidative stress and injuries. In another aspect, $H_2O_2$-mediated boronate oxidation generates free HBA, which exerts its intrinsic antioxidant and anti-inflammatory activities in the tissues undergoing oxidative stress. In other words, the compounds of the invention scavenge $H_2O_2$ and release antioxidant and anti-inflammatory therapeutic agents.

The present invention, which provides $H_2O_2$-activable BRAP and microparticles comprising encapsulated BRAP, e.g., poly(lactic-co-glycolic acid) (PLGA) microparticles, allows for effective lowering of $H_2O_2$ level only when there is overproduction of $H_2O_2$, and spare general $H_2O_2$ suppression in a normal physiological setting. Thus, the targeted strategy of the invention is effective in reducing deleteriously high $H_2O_2$ concentrations and also limits undesirable potential side effects.

Oxidative Stress

Oxidative stress injury occurs when there is an increased production of oxidizing species simultaneously with a reduction in anti-oxidant defenses, resulting in the manifestation of reactive oxygen species (ROS). This overwhelms the cellular defense system and subsequently damages normal cellular functions that can ultimately lead to death (e.g., apoptotic cell death).

In particular, hydrogen peroxide ($H_2O_2$), the most abundant form of the ROS produced during ischemia/reperfusion (I/R), plays an important role by inducing the release of pro-inflammatory cytokines and apoptosis, which further potentiate tissue damage. Hydrogen peroxide is also a precursor of other highly toxic ROS such as hydroxyl radical, peroxinitrite and hypochlorite. Oxidative stress and inflammation events associated with accumulation of $H_2O_2$ are highly correlated with the onset and development of various pathological conditions such as ischemia-reperfusion (I/R) injury.

I/R injuries are seen in a variety of clinical conditions, such as acute coronary syndrome, hepatic and renal ischemic insults, cardiopulmonary bypass surgery and vascular thromboembolic events. Reperfusion of blood flow in ischemic tissues induces a large generation of $H_2O_2$, which causes oxidative stress and cellular damage, further exacerbating tissue damage.

Since the amount of tissue damage is the most important determinant of morbidity and mortality associated with ischemic diseases, limiting cellular death is a paramount approach for favorable outcome in these conditions. Excess amount of $H_2O_2$ that exceeds local anti-oxidant capacity determines the susceptibility for oxidative damage. Therefore, focusing locally on $H_2O_2$ production is a therapeutically relevant way that could stop oxidative stress injury in a variety of disease pathologies. However, the beneficial effects of general anti-oxidant therapy in human clinical studies have been disappointing. One of the main reasons for this lack of benefits in the clinical setting may be due to the fact that non-specific suppression of ROS is not desirable. Although overproduction of $H_2O_2$ (in micromole ranges) during I/R injury is deleterious, $H_2O_2$ at very low levels (in nanomoles) is essential for cellular signaling for normal physiological cellular functions.

In 2011 nearly 11% of US adults had been diagnosed with cardiovascular disease, where more than 50% will also experience co-morbidities such as hypertension and stroke. Although cardiovascular disease has diverse etiology, the primary induction of disease onset is atherosclerosis, the occlusion of primary vessels that carry blood supply to and from the heart. As the disease progresses there will be continued blockage of the arteries leading to necessary procedures such as cardiopulmonary bypass surgery (CPB) or coronary artery bypass graft (CABG), whereby new vessels are either diverted or created in order to bypass those already occluded with plaque allowing for improved circulation. Nearly 2% of US adults, or 395,000 individuals, require a CABG procedure annually in order to forgo life-threatening events such as cardiac arrest.

CABG is a major surgical procedure that requires lengthy hospital stays and likely results in post-operative ischemia or reperfusion-related complications. Complications associated with oxidative damage during CABG (with respective % incidence) include, but are not limited to, atrial fibrillation (up to 40%), infarct extension: reocclusion of an infarct-related artery (IRA) (5-30%), recurrent infarction (17-25%), arrhythmia (13.6%), renal function decrease (5-10%), stroke (6.1%), small-to-moderate MI (2-4%), ventricular tachycardia/fibrillation (2-3%), congestive heart failure (2.4%), GI dysfunction (2.3%), and acute renal failure (0.7%).

Nearly 15% of those patients develop perioperative complications, specifically ischemia and/or reperfusion injury, adding at least an additional $10,000 per patient. Adding insult to injury, one of the main pathogenic mechanisms following CABG surgery is subsequent I/R injury, which can appear as re-occlusion of an infarct-related artery (IRA). Approximately 5-30% of patients experience infarct extension and 17-25% of patients likely experience early IRA. Patients who experience I/R can also clinically present symptoms that include arrhythmias (13.6%) combined with myocardial and microvascular stunning, and hemorrhage (5.6%) often being indistinguishable from the initial injury. Moreover, myocardial necrosis, a clear result of I/R, has been present in a majority of CPB patients with fatal outcome.

The anti-oxidant compounds of the present invention (e.g., 4-(hydroxymethyl)phenylboronic ester) are generally useful for the treatment and/or prevention of diseases and disorders associated with reactive oxygen species and ischemia-reperfusion (I/R) injury.

In certain embodiments, the compounds of the invention provide desired pharmacological effects with temporal and spatial control of therapeutic activities. In other embodiments, the compounds of the invention allow for a target area specificity and a stimuli sensitivity, which enhances the effectiveness of the compounds as well as simultaneously decrease the undesirable side effects. Although most ROS are extremely short lived, $H_2O_2$ is the most stable ROS produced. Consequently, the concentration of $H_2O_2$ tends to accumulate in high level during oxidative stress resulting in cellular damage. The ability of BRAP to react only with $H_2O_2$ allows it to be activated specifically by a pathologic overproduction of $H_2O_2$, as seen during I/R injury, and spare healthy regions.

HBA, one of major active components of *Gastrodia elata*, plays protective roles against brain ischemic injury and coronary artery diseases. In certain embodiments, BRAP is a $H_2O_2$-activable prodrug of HBA, wherein $H_2O_2$-mediated boronate oxidation acts as a chemoselective approach to react with and scavenge $H_2O_2$ in complex biological systems. BRAP with a self-immolative boronic ester protecting group rapidly scavenges $H_2O_2$ and releases therapeutic HBA. Without wishing to be limited by any theory, this property allows BRAP to exert synergistically potent anti-oxidant and anti-inflammatory effects in tissues that are undergoing oxidative stress in a targeted manner. In addition, masking of HBA by boronic ester bond also makes it biocompatible and increases the water solubility, allowing for wider pharmaceutical applications. As demonstrated herein, BRAP is stable in acidic environment, and this allows for its development as an orally bioavailable drug.

As described herein, through the use of mouse hepatic and cardiac I/R injury models, BRAP was shown to effectively reduce oxidative stress, inflammatory response, and initiation of apoptosis. In addition, administration of high doses of BRAP daily for 7 days showed no renal or hepatic function abnormalities, and histological analysis also demonstrated excellent safety profiles. These beneficial effects of BRAP subsequently resulted in decreased organ damages and improved functions. Thus, $H_2O_2$-activable BRAP is a highly potent targeted therapeutic agent for I/R injuries.

In certain embodiments, the compounds of the invention are soluble in aqueous media. In other embodiments, the compounds of the invention are poorly soluble or insoluble in aqueous media.

Figure 18A:
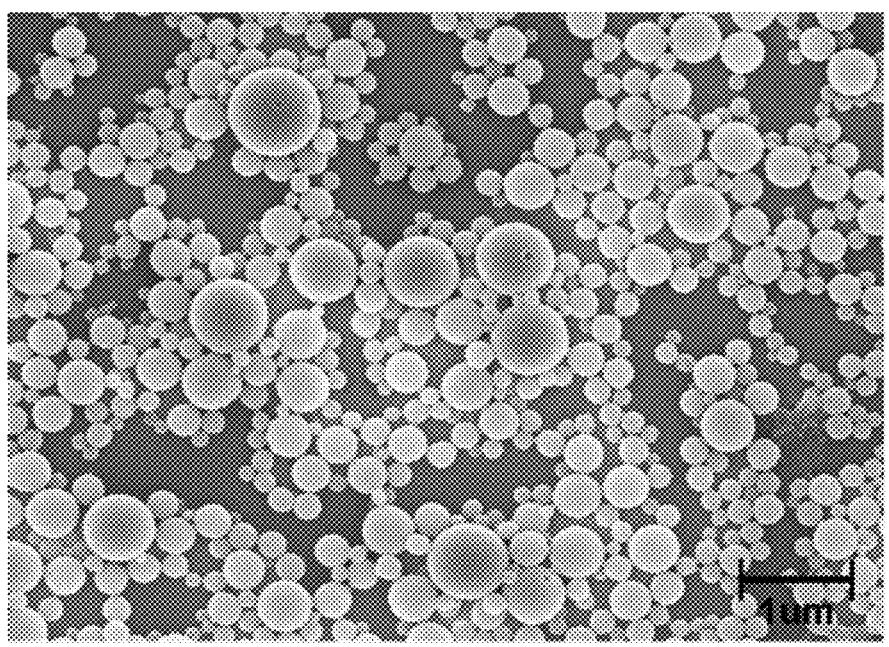
FIGS. 18A and 18B, illustrates aspects of BRAP-encapsulated poly(lactic-co-glycolic acid) (PLGA) microparticles.

In certain embodiments, the compounds of the invention are comprised within microparticles. In other embodiments, the microparticles of the invention are non-toxic, biocompatible and degraded under physiological conditions. In yet other embodiments, the microparticles of the invention comprise poly(lactic acid) (PLA), poly(glycolic acid) (PGA), poly(lactic-co-glycolic acid) (PLGA), poly(ε-caprolactone) (PCL), or any combinations thereof. In a particular embodiment, the microparticles comprise PLGA and encapsulate BRAP (See, e.g., FIGS. 18A and 18B). The microparticles of the invention are useful to hold and/or release the anti-oxidant and/or anti-inflammatory compounds and/or compositions of the invention.

Disclosure

The invention includes a boronic ester, wherein the boronic ester is capable of reacting, at least partially, with hydrogen peroxide to form an anti-inflammatory and/or anti-oxidant compound. In certain embodiments, the boronic ester comprises a 4-(hydroxymethyl) phenylboronic ester. In other embodiments, the anti-inflammatory and/or anti-oxidant compound comprises a phenolic compound. In yet other embodiments, the phenolic compound comprises 4-hydroxybenzyl alcohol (HBA).

The boronic ester comprises an alcohol and a boronic acid, wherein the boronic acid and the alcohol are covalently conjugated to form the boronic ester. In certain embodiments, the boronic acid is aromatic. In other embodiments, the boronic acid comprises 4-(hydroxymethyl) phenylboronic acid. In other embodiments, the alcohol is a diol, triol, tetraol, pentaol, hexaol or a higher polyol. In yet other embodiments, the alcohol is a diol or a triol. In yet other embodiments, the diol comprises 1,3-propanediol. In yet other embodiments, the boronic ester comprises BRAP. In yet other embodiments, the triol comprises 2-(hydroxymethyl)-2-methylpropane-1,3-diol. In yet other embodiments, the boronic ester comprises (4-(1,3,2-dioxaborinan-2-yl) phenyl)methanol. In yet other embodiments, the alcohol is non-toxic to and biocompatible with a subject. In yet other embodiments, the subject is a mammal.

In certain embodiments, the boronic ester may be prepared by contacting the alcohol and the boronic acid in a nonaqueous solvent, such as tetrahydrofuran, dichloromethane or dimethylformamide. The resulting boronic ester may be purified using methods known to those skilled in the art, such as but not limited to extraction, crystallization, precipitation, chromatography, and the like.

In certain embodiments, the boronic esters of the invention are part of a pharmaceutical composition.

In certain embodiments, the boronic esters of the invention are comprised within microparticles. In yet other embodiments, the microparticles comprise at least one polymer. In yet other embodiments, the polymer is selected from the group consisting of poly(lactic acid) (PLA), poly(glycolic acid) (PGA), poly(lactic-co-glycolic acid) (PLGA), poly(ε-caprolactone) (PCL), and any combinations thereof. In yet other embodiments, the microparticles comprise liposomes. In yet other embodiments, the microparticles are non-toxic and biocompatible, and are degraded under physiological conditions while releasing an anti-inflammatory and/or anti-oxidant compound, such as HBA, which has anti-oxidant and anti-inflammatory effects. The microparticles of the invention are useful as drug delivery systems and components of anti-oxidant or anti-inflammatory compositions.

Figure 18B:
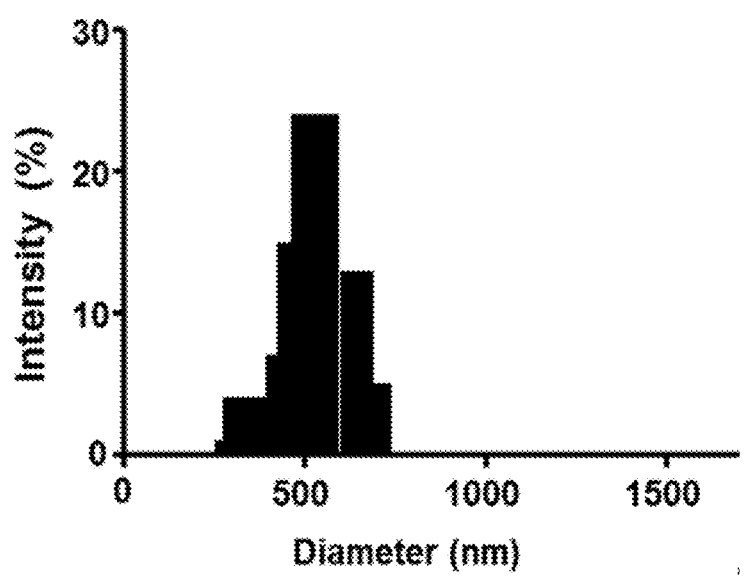

In certain embodiments, the diameter of the microparticles ranges from about 200 to about 20 μm. In yet other embodiments, the diameter of the microparticles ranges from about 200 to about 800 nm. In yet other embodiments, the diameter of the microparticles ranges from about 400 to about 600 nm. (FIG. 18B).

The present invention further includes an anti-oxidant and/or anti-inflammatory pharmaceutical composition, wherein the composition comprises a boronic ester of the invention as an active ingredient.

The present invention further includes a pharmaceutical composition for preventing or treating ischemic disease, wherein the composition comprises a boronic ester of the invention as an active ingredient.

Non-limiting examples of ischemic diseases contemplated within the invention include brain ischemia, heart ischemia, diabetic cardiovascular diseases, heart failure, myocardial hypertrophy, retinal ischemia, ischemic colitis, critical limb ischemia, ischemic acute renal failure, stroke, brain trauma, fetal hypoxia, glaucoma, diabetic neuropathy, ischemia/reperfusion injury or ischemia/reperfusion injury complications, and whole body ischemia/reperfusion, such as cardiac arrest resuscitation.

In one embodiment, the ischemia/reperfusion injury is associated with cardiopulmonary bypass (CPB) surgery. In another embodiment, ischemic injury is associated with coronary arterial bypass graft (CABG) surgery; valve, defect or aneurysm repair; heart, lung, kidney, liver and/or pancreas transplantation; pulmonary thrombectomy; or pulmonary thromboendarterectomy.

In one embodiment, compounds of the invention are useful for the treatment of complications associated with CPB (and/or CABG) surgery (e.g., atrial fibrillation, infarct extension, with reocclusion of an infarct-related artery (IRA), recurrent infarction, arrhythmia, renal function decrease, stroke, small-to-moderate MI, ventricular tachycardia/fibrillation, congestive heart failure, GI dysfunction and acute renal failure).

The present invention further includes a pharmaceutical composition for preventing or treating a ischemic injury associated with solid organ transplantation (such as liver, kidney, lung or heart) or solid organ preservation (such as liver, kidney, lung or heart), wherein the composition comprises a boronic ester of the invention as an active ingredient.

The pharmaceutical compositions of the present invention may contain at least one known active ingredient having an anti-oxidant effect, an anti-inflammatory effect, or the effect of preventing or treating ischemic injury.

Organ or Tissue Transplantation

The invention features improved methods for organ or tissue transplantation. Ischemic damage and reperfusion injury reduces the viability of cells, tissues, or organs available for transplantation. The invention provides compositions that reduce such injury. Preferably, a composition of the invention is administered to a tissue or organ (donor organ or tissue), including but not limited to, cardiac tissue, heart, kidney tissue, kidney, hepatic tissue, liver, lung tissue, lung, pancreatic tissue, pancreas, intestine tissue, intestine, thymus, bone, cartilage, muscular tissue, tendon, cornea, epithelial tissue, skin, cardiac valve, neurons, nerves, endothelial tissue, artery, or vein, prior to, during, or after transplantation. Methods for organ transplantation are known in the art.

Methods

In one aspect, the invention includes a method of treating or preventing a disease associated with inflammation or a reactive oxygen species in a subject in need thereof. In one embodiment, the method comprises administering to the subject a therapeutically effective amount of a boronic ester of the invention, wherein the ester undergoes at least partial degradation to release an anti-inflammatory and/or anti-oxidant compound within the body of the subject.

In another aspect, the invention includes a method of inhibiting or preventing the formation of reactive oxygen species (ROS) in at least one bodily site of a subject, wherein the method comprises administering to the subject a therapeutically effective amount of a boronic ester of the invention, wherein the ester undergoes at least partial degradation to release an anti-inflammatory and/or anti-oxidant compound within the body of the subject, and, whereby the formation of ROS in at least one bodily site of the subject is inhibited or prevented.

In still another aspect, the invention includes a method for reducing ischemic damage or reperfusion injury in a tissue or organ for transplantation, the method comprising contacting the tissue or organ with a boronic ester of the invention, during or after transplantation, wherein the ester undergoes at least partial degradation to release an anti-inflammatory and/or anti-oxidant compound, thereby reducing ischemic damage or reperfusion injury in the tissue or organ.

Formulations/Administration

The compositions of the present invention may contain a pharmaceutical acceptable carrier, excipient and/or diluent, and may be administered by a suitable method to a subject. The compositions of the present invention may be formulated in various forms, including oral dosage forms or sterile injectable solutions, according to any conventional method known in the art. In addition, the compositions may also be used as an inhalation-type drug delivery system. In one embodiment, the compositions of the invention may be formulated as solid nanopowder.

The compositions may be formulated as powders, granules, tablets, capsules, suspensions, emulsions, syrup, aerosol, preparations for external application, suppositories and sterile injectable solutions. Suitable formulations known in the art are disclosed in, for example, Remington's Pharmaceutical Science (Mack Publishing Company, Easton Pa.). Carriers, excipients and diluents that may be contained in the composition of the present invention include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propyl hydroxylbenzoate, talc, magnesium stearate or mineral oil.

The compositions of the present invention may be formulated with commonly used diluents or excipients, such as fillers, extenders, binders, wetting agents, disintegrants, or surfactants. Solid formulations for oral administration include tablets, pills, powders, granules, or capsules, and such solid formulations comprise, in addition to the composition, at least one excipient, for example, starch, calcium carbonate, sucrose, lactose or gelatin. In addition to simple excipients, lubricants such as magnesium stearate or talc may also be used. Liquid formulations for oral administration include suspensions, solutions, emulsions and syrup, and may contain various excipients, for example, wetting agents, flavoring agents, aromatics and preservatives, in addition to water and liquid paraffin, which are frequently used simple diluents.

Formulations for parenteral administration include sterilized aqueous solutions, non-aqueous solutions, suspensions, emulsions, freeze-dried preparations, and suppositories. As non-aqueous solvents or suspending agents, propylene glycol, polyethylene glycol, plant oils such as olive oil, or injectable esters such as ethyl oleate may be used. As the base of the suppositories, witepsol, Macrogol, Tween 61, cacao butter, laurin fat, or glycerogelatin may be used.

The preferred dose of the pharmaceutical compositions of the present invention varies depending on the patient's condition and weight, the severity of the disease, the type of drug, and the route and period of administration and may be suitably selected by those skilled in the art. For preferred effects, the pharmaceutical composition of the present invention may be administered at a dose of 0.01-100 mg/kg/day. The composition may be administered once or several times a day.

The compositions of the present invention may be administered to a subject by various routes. All modes of administration are contemplated, for example, orally, rectally or by intravenous, intramuscular, subcutaneous, intracutaneous, intrauterine, epidural or intracerebroventricular injection.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Figure 1B:
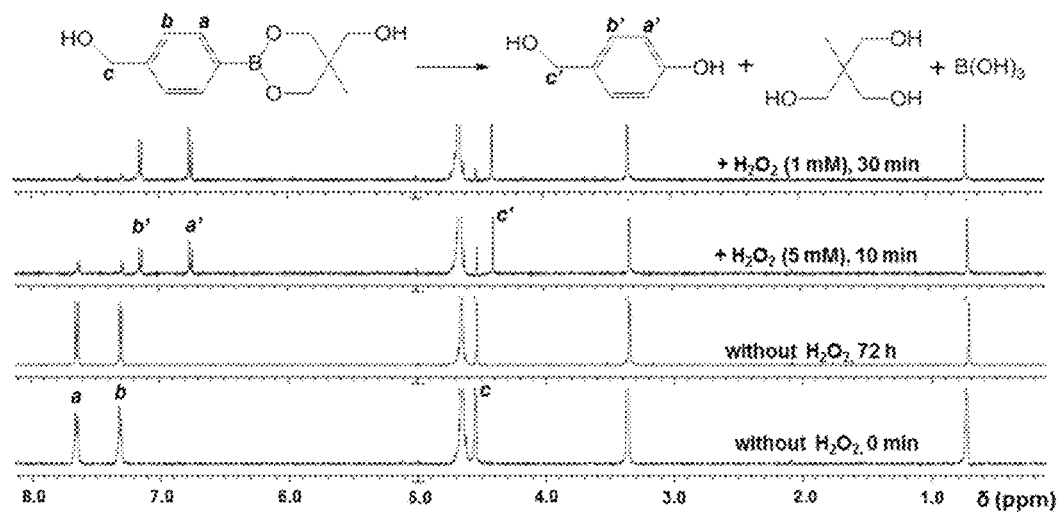

Example 1: Synthesis of BRAP $H_2O_2$-activable anti-oxidant prodrug BRAP was synthesized by reacting (4-(hydroxymethyl)phenyl)boronic acid and 2-(hydroxymethyl)-2-methylpropane-1,3-diol at room temperature (FIG. 1A). BRAP was obtained as white water-soluble powder and its chemical structure was confirmed by $^1$H NMR (FIG. 1B).

Example 2: Reaction of BRAP with Hydrogen Peroxide

Since BRAP was designed to be rapidly oxidized by $H_2O_2$, generating HBA, boric acid and 2-(hydroxymethyl)-2-methylpropane-1,3-diol, the sensitivity of BRAP to $H_2O_2$ was investigated using $^1$H NMR. BRAP was added to $D_2O$ containing $H_2O_2$ and the changes in the signal were monitored over time. In the presence of $H_2O_2$, BRAP was rapidly oxidized to generate HBA in a $H_2O_2$ concentration-dependent manner, confirmed by the appearance of new aromatic proton peaks at 6.8 and 7.2 ppm. In the presence of equimolar concentration of $H_2O_2$ (1 mM), a majority of boronic esters were cleaved within 30 minutes, with a half-life of hydrolysis of ~5 minutes. Nearly all of boronic ester groups were cleaved by 5-fold excess of $H_2O_2$ (5 mM) within 5 minutes. However, in the absence of $H_2O_2$, the boronic ester remained intact even after 3 days.

Figure 2A:
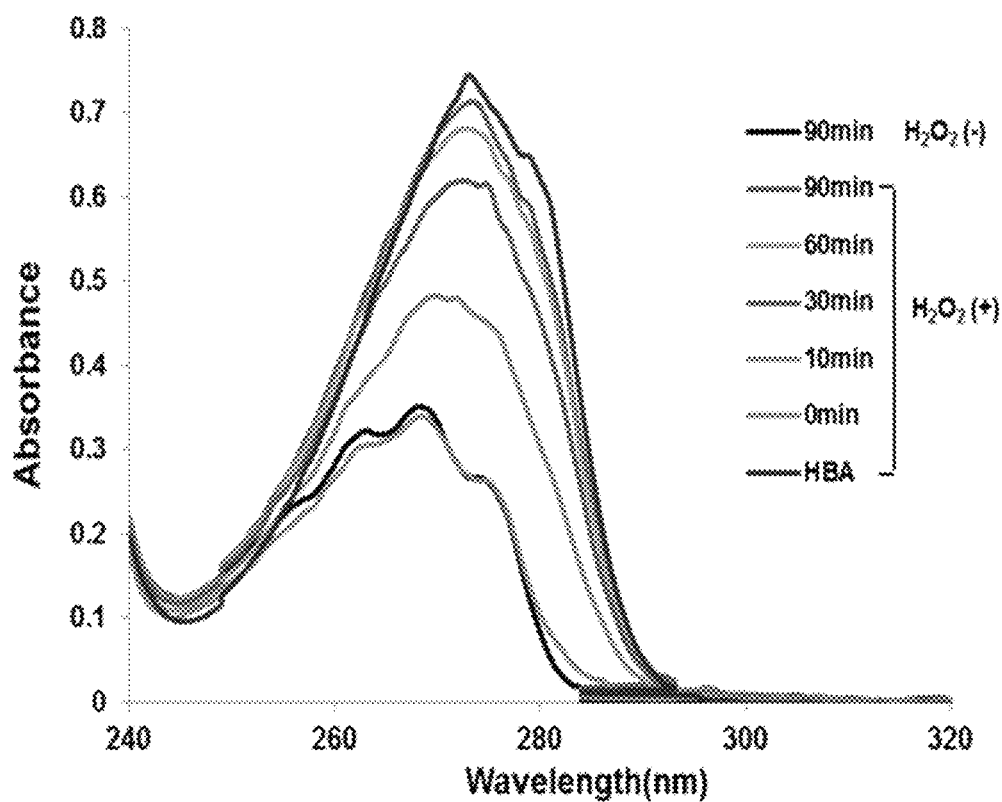
FIGS. 2A-2C, illustrates $H_2O_2$ scavenging effects of BRAP.

The activation of BRAP by $H_2O_2$ was also studied using UV spectroscopy. BRAP was mixed with $H_2O_2$ and the change in UV absorbance was monitored over time. The absorbance at 273 nm was increased over time because of the appearance of the phenolic hydroxyl group of HBA, demonstrating the expected cleavage of boronic esters and generation of HBA (FIG. 2A). After 90 minutes of treatment, BRAP showed no further increase in UV absorbance and its UV absorbance intensity was almost the same as those of the same concentration of HBA.

Figure 2B:
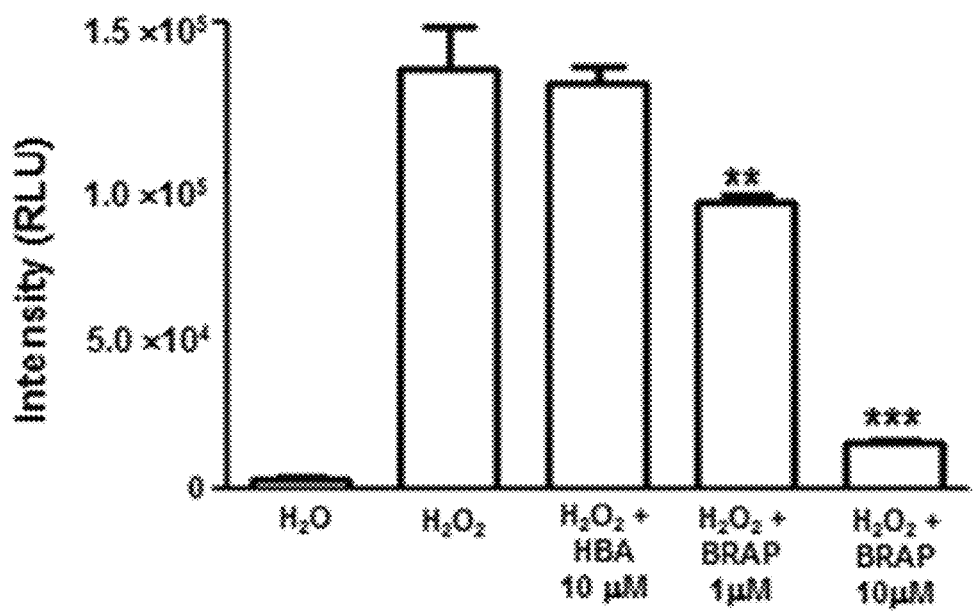
Figure 2C:
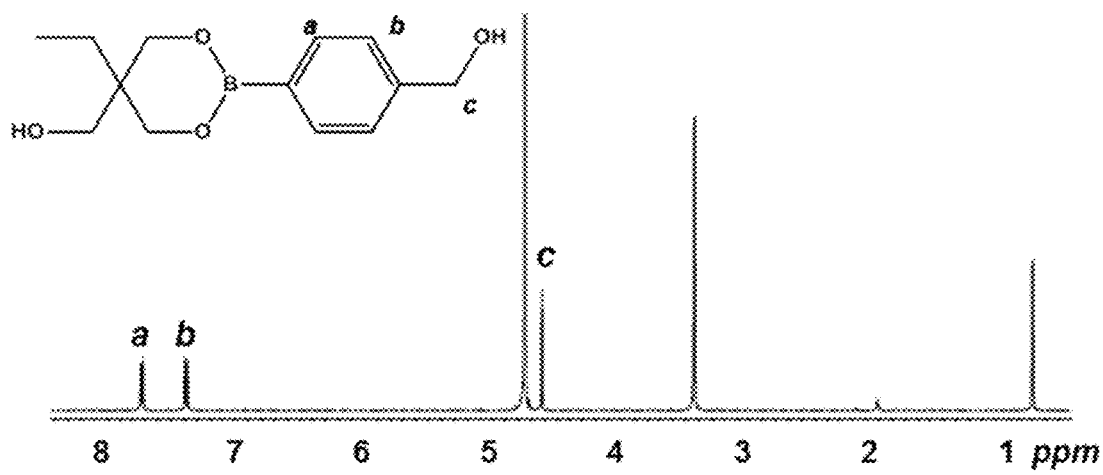
Figure 3A:
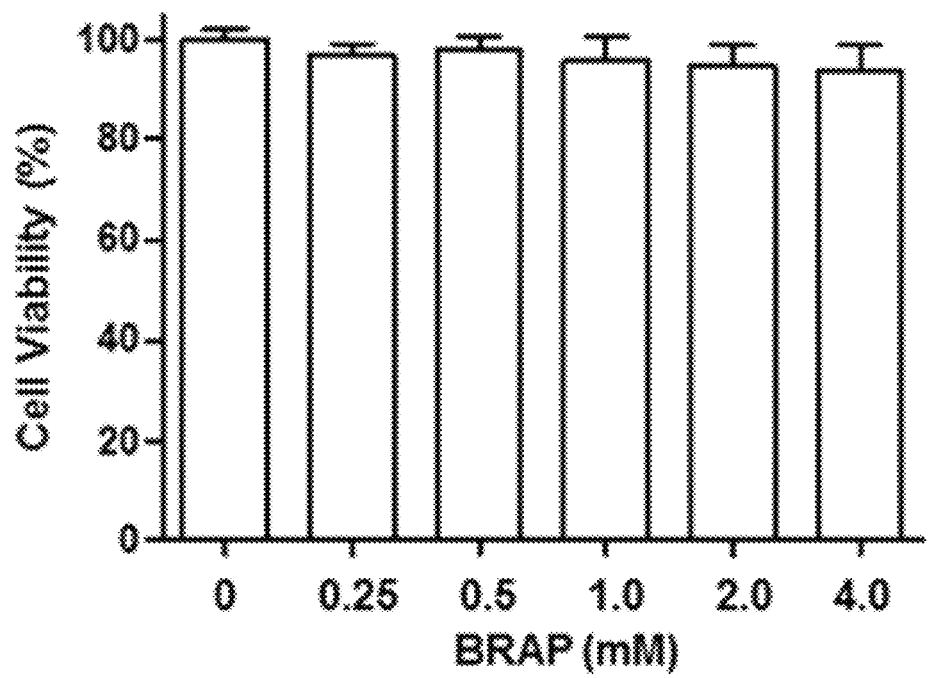
FIGS. 3A-3B, is a set of bar graphs illustrating biocompatibility profiles of BRAP assessed by MTT assay in mouse macrophage (RAW264.7) cells (FIG. 3A) and ARVC (FIG. 3B).
Figure 3B:
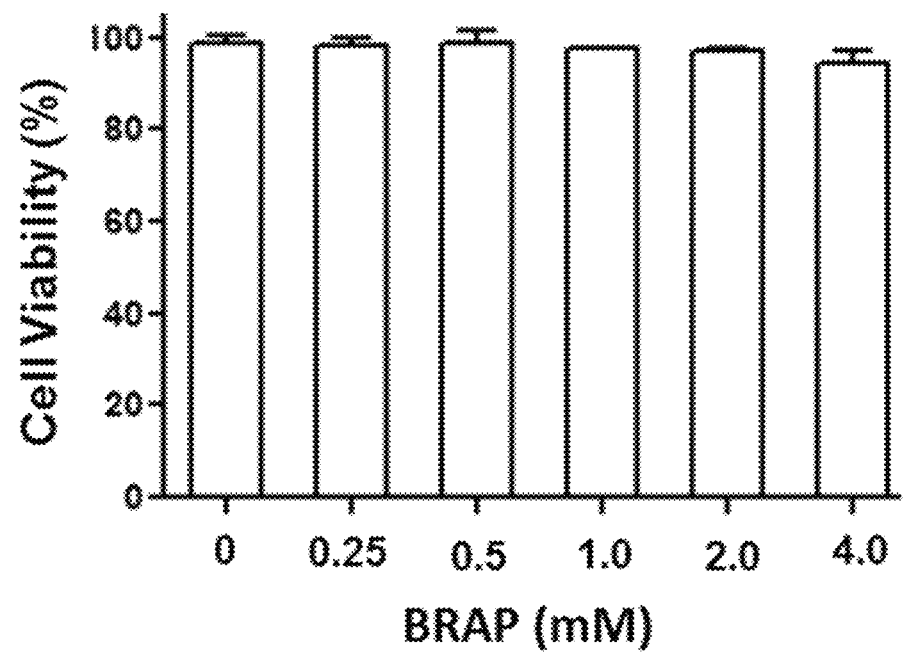
Figure 21:
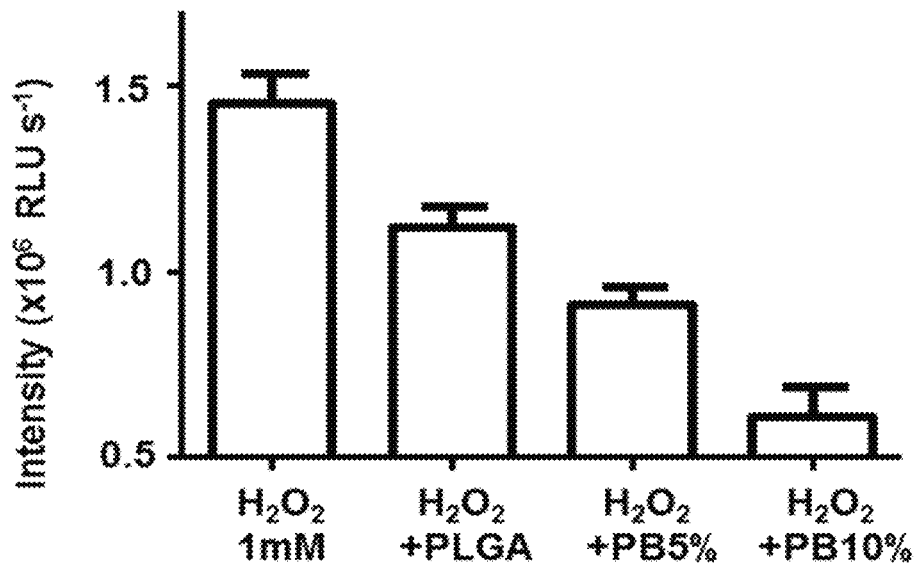
FIG. 21 is a bar graph illustrating $H_2O_2$-scavenging by BRAP-encapsulated PLGA microparticles. BRAP-encapsulated PLGA microparticles were incubated in $H_2O_2$ solution (10 μM) for 10 minutes, and the level of $H_2O_2$ was determined by peroxalate chemiluminesce using rubrene (1 mg) and diphenylperoxalate (10 mg).

Without wishing to be limited by any theory, BRAP could scavenge $H_2O_2$ during its $H_2O_2$-mediated boronate oxidation. This possibility was investigated using peroxalate chemiluminescence. Peroxalate chemiluminescence has been used as a versatile tool for the detection of a variety of chemical species including fluorescent molecules and $H_2O_2$ because of its excellent specificity and simplicity (Hadd, et al., 1999, J. Chem. Educ. 76:1237; Lee, et al., 2011, Bull. Korean Chem. Soc. 32:2187). The pure $H_2O_2$ solution showed remarkably high emission intensity (~$1.3 \times 10^5$ RLU). The addition of BRAP resulted in significant reduction in chemiluminescence intensity, in a concentration-dependent manner (FIG. 2B and FIG. 21). A majority of $H_2O_2$ was scavenged by the same concentration of BRAP within 1 minutes. In contrast, HBA alone (10 μM) did not reduce chemiluminescence intensity. These observations demonstrate that BRAP rapidly reacts with $H_2O_2$ to render efficient elimination of $H_2O_2$. In addition, the stability of BRAP was not influenced by acidic environments (pH 3.0) during the 72 hours of incubation (FIG. 2C).

Example 3: Cytotoxicity of BRAP

Figure 19:
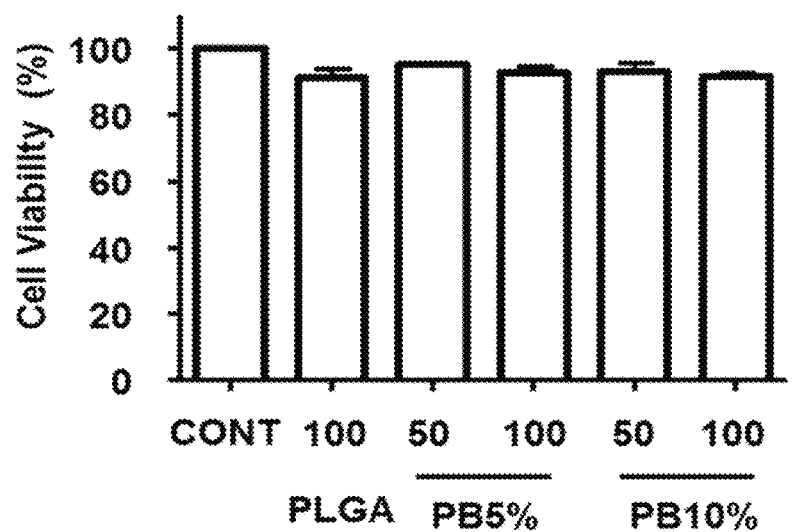
FIG. 19 is a bar graph showing the results of assessing cytotoxicity of BRAP-encapsulated PLGA microparticles against RAW264.7 cells in vitro. Cell viability was determined by the 3-(4,5-dimethylthiazil-2yl)-2,5-diphenyltetrazolium bromide (MTT) assay 24 hours after addition of BRAP-encapsulated PLGA microparticles to cells. "PB" represents BRAP-encapsulated PLGA microparticles. The percentages indicate the weight content of BRAP in the particles. Values shown represent mean±s.d. (n=4). As observed from the results, BRAP-encapsulated PLGA microparticles do not adversely affect cell viability.
Figures 20A, 20B, 20C, 20D, 20E:
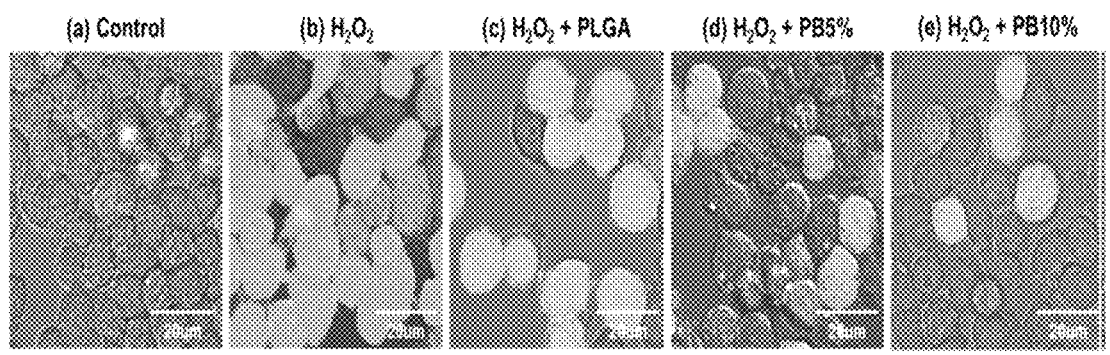
FIGS. 20A-20E, shows photomicrographic images of $H_2O_2$-stimulated RAW264.7 cells treated with BRAP-encapsulated PLGA microparticles. The cells were stimulated with $H_2O_2$ and treated with BRAP-encapsulated PLGA microparticles. The intracellular generation of reactive oxygen species (ROS) was visualized with dihydrodichlorofluorescein-diacetate (DCFH-DA) as a probe for ROS.

Initial cytotoxicity experiments of BRAP demonstrated no significant cytotoxicity at concentrations as high as 5 mM after 24 hours of incubation in various cell lines and primary culture of adult rat ventricular cardiomyocytes (ARVC) in vitro (FIGS. 3A-3B and 8A, 8B and 18). Similarly, no significant cytotoxicity was demonstrated following treatment of RAW264.7 cells with BRAP-encapsulated PLGA microparticles containing 5% BRAP, by weight (PB5%) and 10% BRAP, by weight (PB10%), (FIG. 19).

Example 4: Anti-Oxidant Properties of BRAP

Figure 4A:
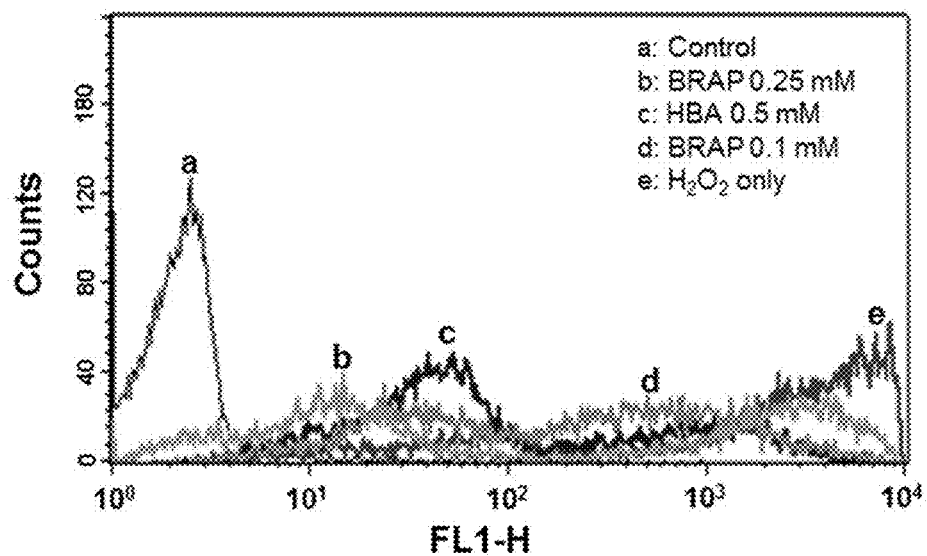
FIGS. 4A-4F, is a set of graphs, bar graphs and images illustrating anti-oxidant and anti-inflammatory effects of BRAP in vitro.
Figure 4B:
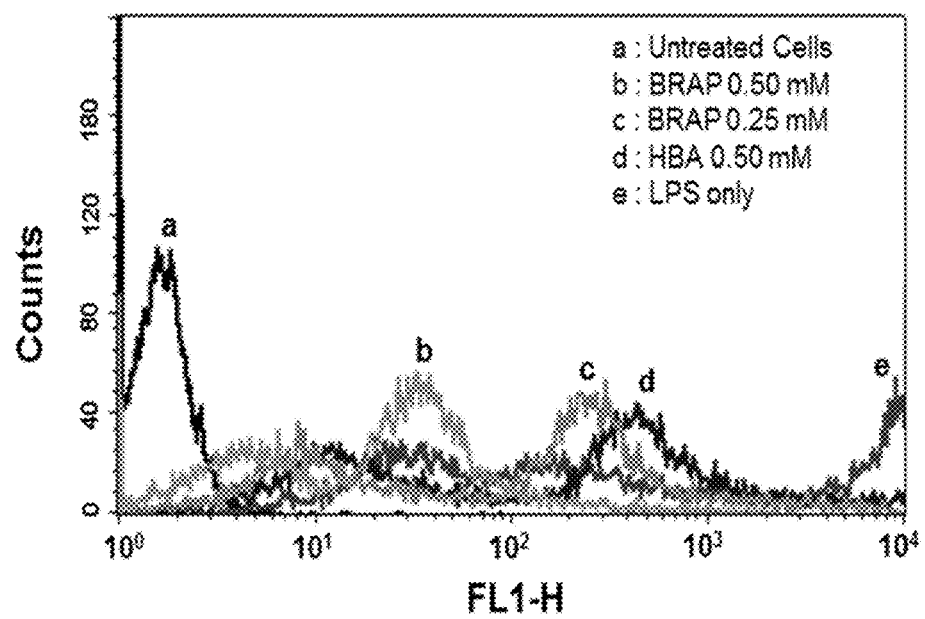

The anti-oxidant activities of BRAP were examined using mouse macrophage (RAW 264.7) and fibroblast (NIH/3T3) cells stimulated by LPS (lipopolysaccharide) (FIGS. 4A-4B). Intracellular ROS production in the stimulated cells was analyzed by flow cytometry using DCFH-DA (dihydrodichlorofluorescein-diacetate), which can be oxidized by the action of various intracellular oxidants such as $H_2O_2$ and hydroxyl radical to become fluorescent dihydrodichlorofluorescein (DCF) (Kim, et al., 2011, Biomat. 32:3021; Cho, et al., 2012, Adv. Funct. Mat. 22:4038). Untreated cells have no significant DCF fluorescence. On the other hand, strong DCF fluorescence was observed in the cells treated with exogenous LPS because LPS induced the generation of ROS which oxidized DCFH-DA to fluorescent DCF.

Figure 9:
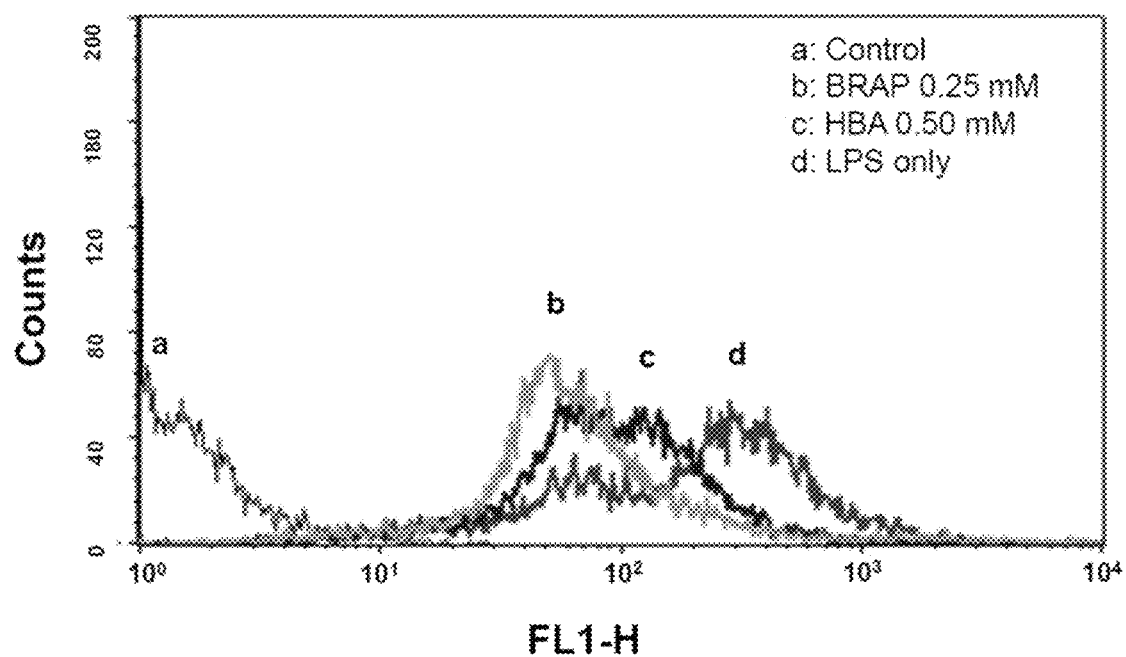
FIG. 9 is a graph illustrating inhibitory effects on ROS generation in mouse embryonic fibroblast (NIH 3T3) cells stimulated by LPS (1 µg/mL).

HBA at 0.5 mM showed moderate inhibitory effects on ROS generation in dose-dependent manners. However, 0.25 mM of BRAP exerted significantly stronger inhibitory effects on the LPS-induced ROS generation than 0.5 mM of HBA. Similar inhibition of LPS-induced ROS generation was observed in the mouse fibroblasts (FIG. 9). Furthermore, BRAP-encapsulated PLGA microparticles demonstrated anti-oxidant effects on $H_2O_2$-stimulated cells (RAW264.7), which were protected against the generation of ROS. (FIGS. 20A-20E).

Figure 4C:
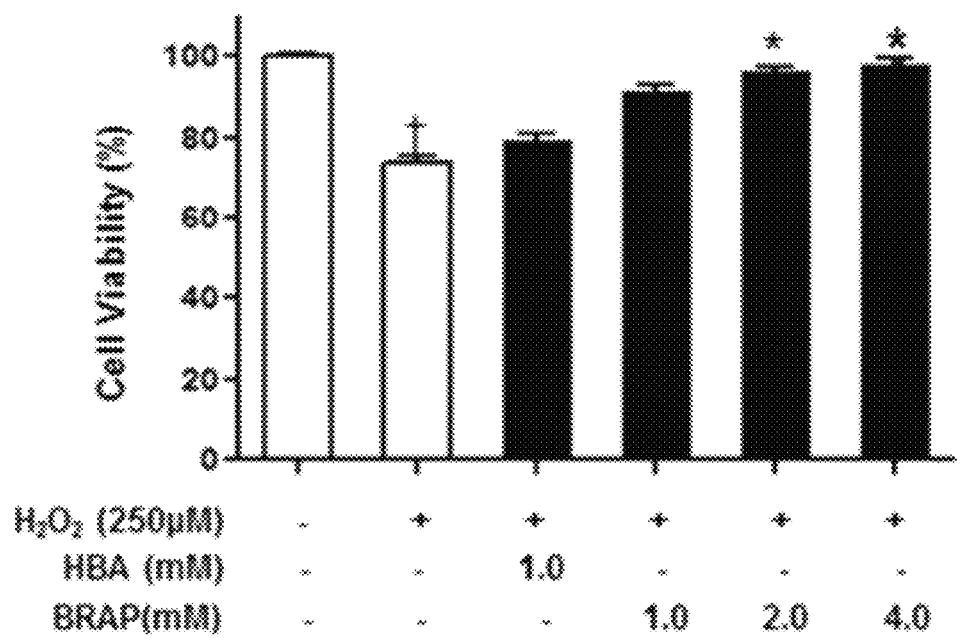
Figure 22:
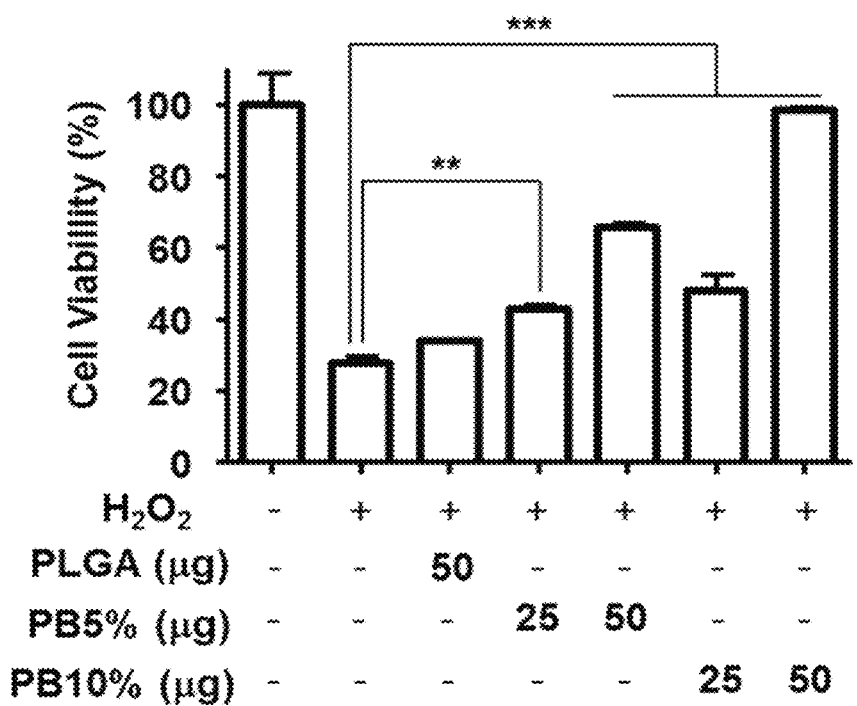
FIG. 22 is a bar graph illustrating the protective activity of BRAP-encapsulated PLGA microparticles against the effects of $H_2O_2$ in $H_2O_2$-stimulated RAW264.7 cells. Cells cultured in 1 mL of medium were activated with 200 μM of $H_2O_2$ for 1 hour and then were treated with BRAP-encapsulated PLGA microparticles. Cell viability was determined by MTT assay at 24 hours post-treatment. Values shown are mean±s.d. (n=4). *P<0.001; P<0.01.

Since cardiovascular disease is one of the most common and clinically relevant problems associated with oxidative stress injury, the effect of BRAP on cellular protection from the $H_2O_2$-induced cell death was further examined using ARVC in vitro. $H_2O_2$ (0.25 mM) resulted in approximately 30% cell death. Compared to this vehicle control, BRAP showed significant protection from $H_2O_2$-induced cell death in a concentration dependent manner (FIG. 4C). In addition, BRAP-encapsulated PLGA microparticles demonstrated protective activity against $H_2O_2$-stimulated cells (RAW264.7) in vitro (FIG. 22).

Example 4: Effect of BRAP on Nitric Oxide Generation

Figure 4D:
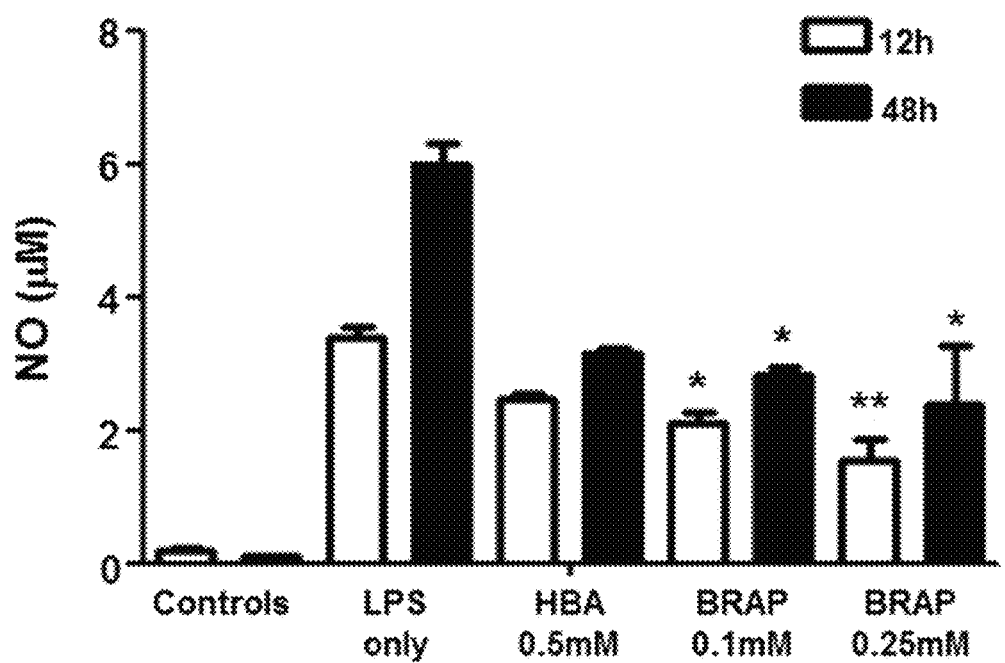

Nitric oxide is one of major sources of oxidative stress and a well-known pro-inflammatory mediator in the pathogenesis of inflammation (Lundberg, et al., 1997, Nature Medicine 3:30). The effects of BRAP on the generation of nitric oxide in LPS-treated cells were studied using a colorimetric assay based on the Griess reaction. LPS induced a large amount of nitric oxide production and BRAP exerted the inhibitory effects on nitric oxide production in time and dose-dependent manners (FIG. 4D). HBA alone also inhibited nitric oxide production, but only at a concentration higher than 0.5 mM, suggesting a superior anti-oxidant activity of BRAP.

Example 5: Anti-Inflammatory Effect of BRAP

Figure 4E:
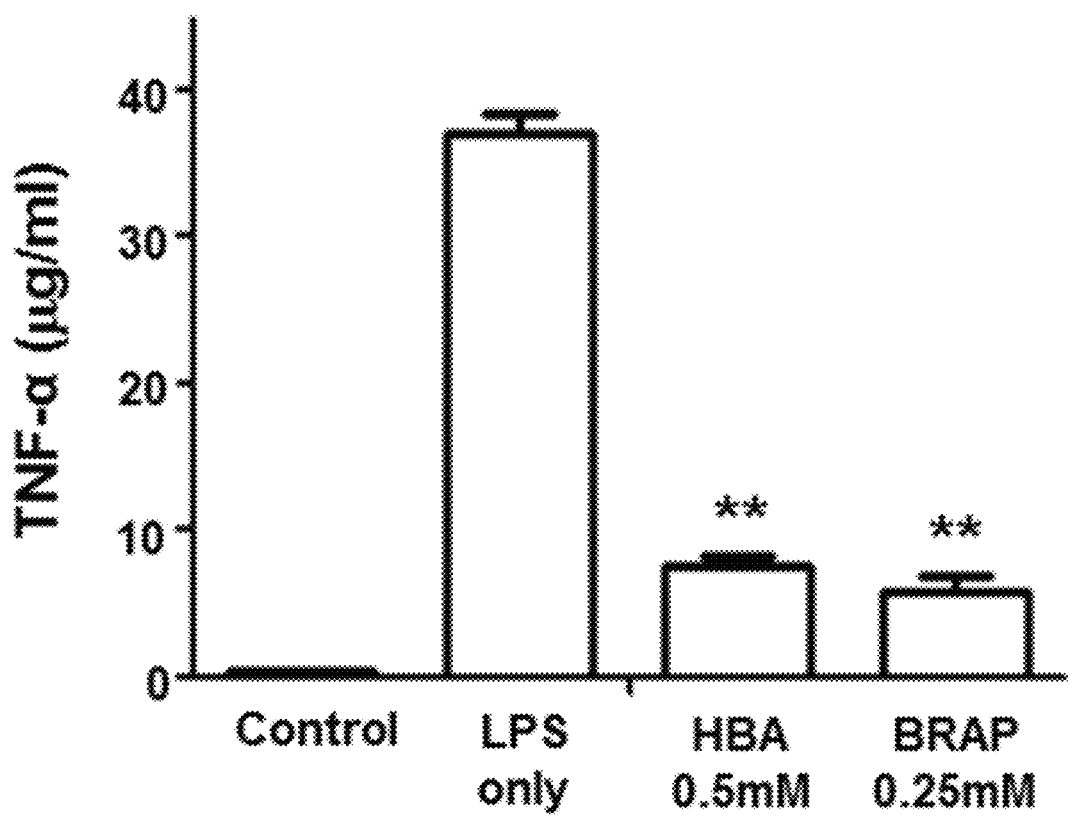
Figure 4F:
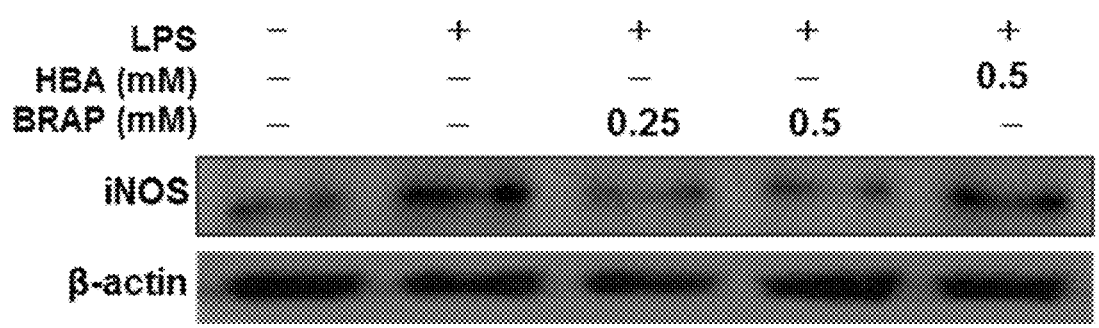
Figure 23:
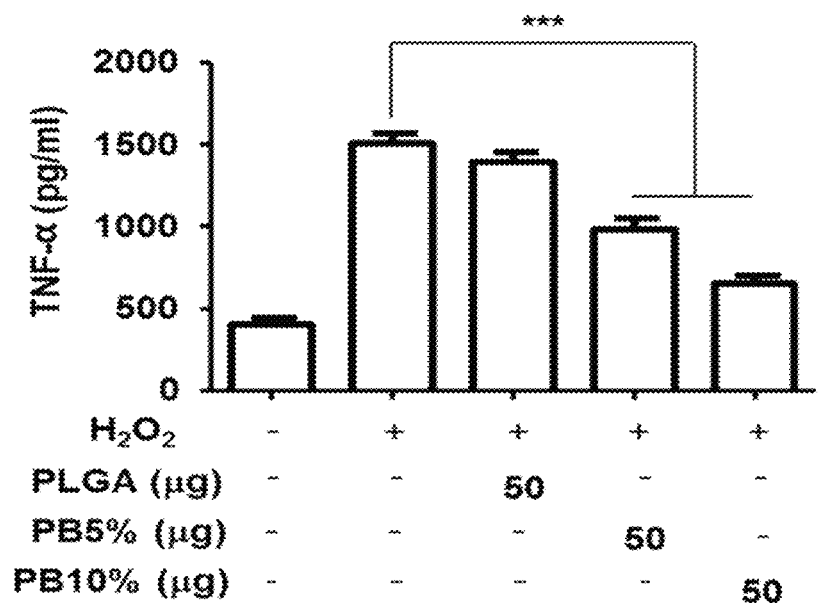
FIG. 23 is a bar graph depicting results of an assay evaluating the effects of BRAP-encapsulated PLGA microparticles on TNF-α expression in $H_2O_2$-stimulated RAW264.7 cells. For the assay, cells cultured in 1 mL of medium were activated with 200 μM of $H_2O_2$ for 1 hour and then BRAP-encapsulated PLGA microparticles were added (50 μg). The level of TNF-α (pg/ml) expressed by the cells was determined at 24 hours post-addition of microparticles. Values shown are mean±s.d. (n=4). ***: P<0.001. The inhibitory effect of the microparticles on TNF-α expression is observed for the cells treated with the microparticles.

The anti-inflammatory effects of BRAP on LPS-stimulated cells were investigated by measuring the level of inflammatory cytokines such as TNF-α (tumor necrosis factor-alpha) and iNOS (inducible nitric oxide synthases) (FIGS. 4E-4F). The level of TNF-α was significantly increased by the LPS treatment. BRAP exhibited strong anti-inflammatory effects by significantly suppressing both TNF-α and iNOS levels. HBA alone also reduced the expression of TNF-α but only at a higher dose than BRAP, and failed to reduce iNOS level even at a higher dose. BRAP-encapsulated PLGA microparticles also inhibited TNF-α expression levels in $H_2O_2$-stimulated cells (RAW264.7) (FIG. 23). These observations indicate that BRAP, as well as BRAP-encapsulated PLGA microparticles, is able to scavenge overproduced $H_2O_2$ and serve as a $H_2O_2$-activable anti-oxidant. Further, the enhanced anti-oxidant activity of BRAP is derived from the combined effects of $H_2O_2$-scavenging boronic esters and HBA generation after $H_2O_2$-mediated boronate oxidation.

Example 6: Anti-Apoptotic and Anti-Inflammatory Effects of BRAP

Figure 5A:
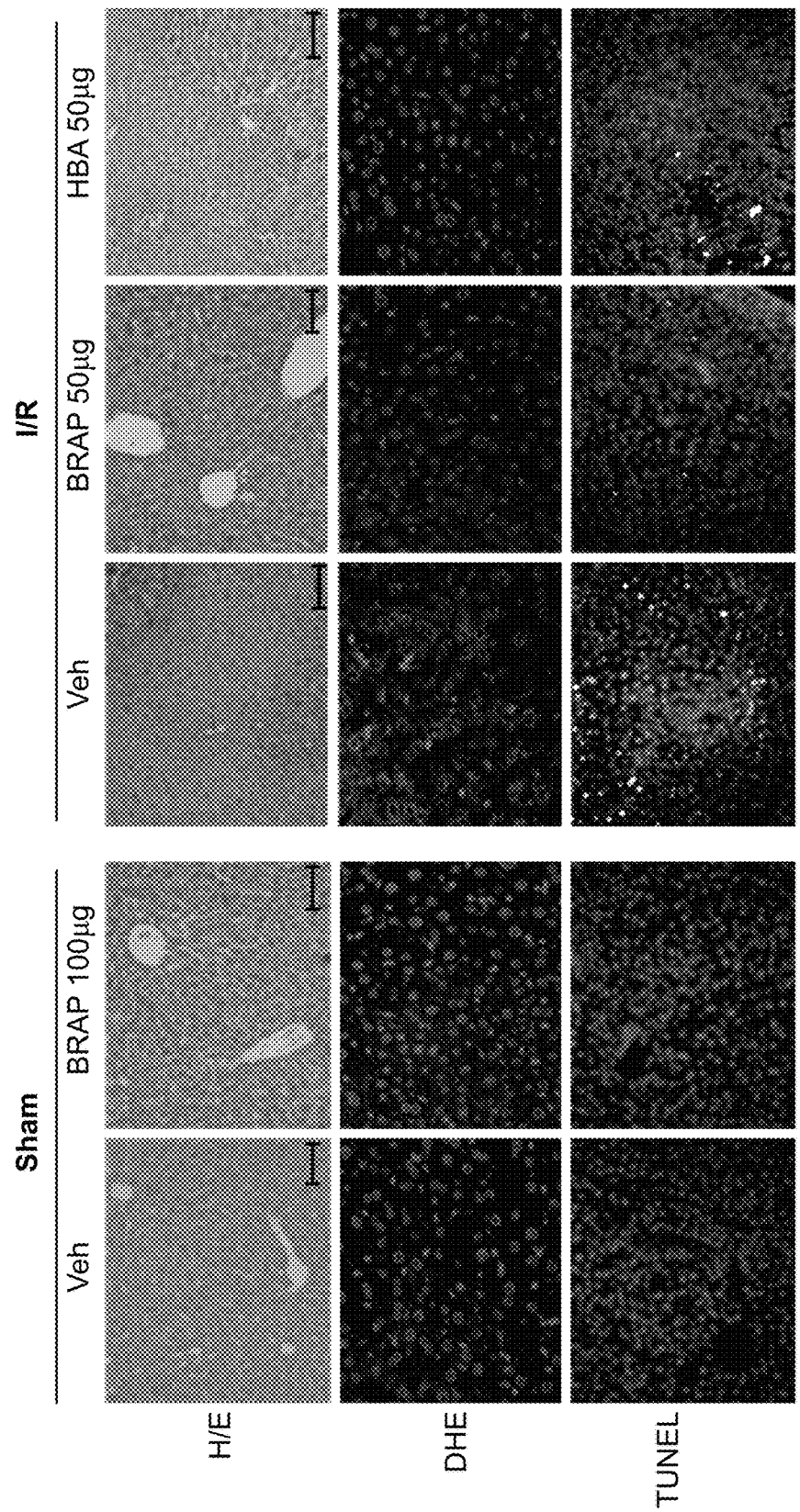
FIGS. 5A-5D, is a set of images and bar graphs illustrating beneficial effects of BRAP in hepatic I/R (1 hour ischemia/12 hour reperfusion) injury.

Experiments to evaluate whether BRAP reduces ROS generation and inhibits apoptosis were performed in a mouse model of hind-limb I/R injuries. I/R was induced first by 1 hour of ligation of hepatic artery and portal vein followed by reperfusion of hepatic artery. BRAP or HBA was then administrated intraperitoneally (ip) at the time of reperfusion. Histological analysis after I/R injury demonstrated hepatic damages, as evidenced by the increased infiltration of inflammatory cells (FIG. 5A).

HBA showed minimal therapeutic effects on hepatic damages during I/R, but the same dose of BRAP resulted in significant attenuation of these tissue damages. In order to investigate the effects of BRAP on ROS generation during I/R injury, tissues were stained with dihydroethidium (DHE), which is permeable into cells and becomes fluorescent in the presence of oxidants including superoxide, $H_2O_2$, and other reactive oxygen.

I/R injury caused a large generation of ROS, evidenced by the strong purple fluorescence. ROS generation was suppressed by both HBA and BRAP, but BRAP exhibited higher inhibitory effects on ROS generation than HBA. I/R injury also caused severe hepatic apoptosis, confirmed by the number of strong TUNEL (Terminal deoxynucleotidyl transferase dUTP nick end labeling) positive cells. HBA exhibited modest inhibitory effects on hepatic apoptosis, whereas the same dose of BRAP showed significantly greater anti-apoptotic effects than HBA.

Figure 5B:
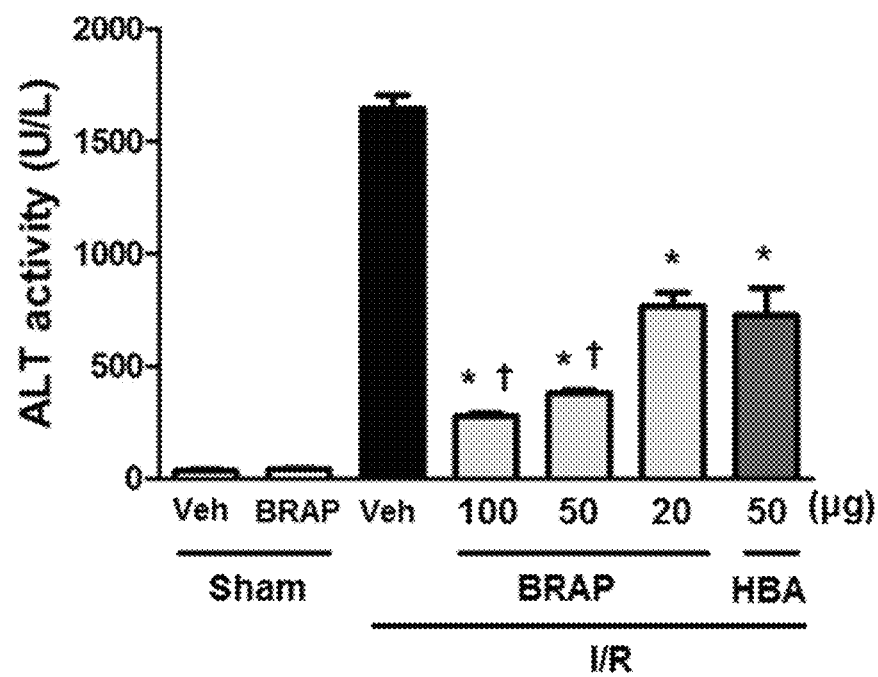

Corresponding to histologic findings, I/R induced a liver damage as measured by the increase in alanine transaminase (ALT) in the serum (FIG. 5B). BRAP demonstrated a concentration-dependent protection from the I/R-induced liver damage. HBA had much less potent protective effect compared to BRAP.

Figure 5C:
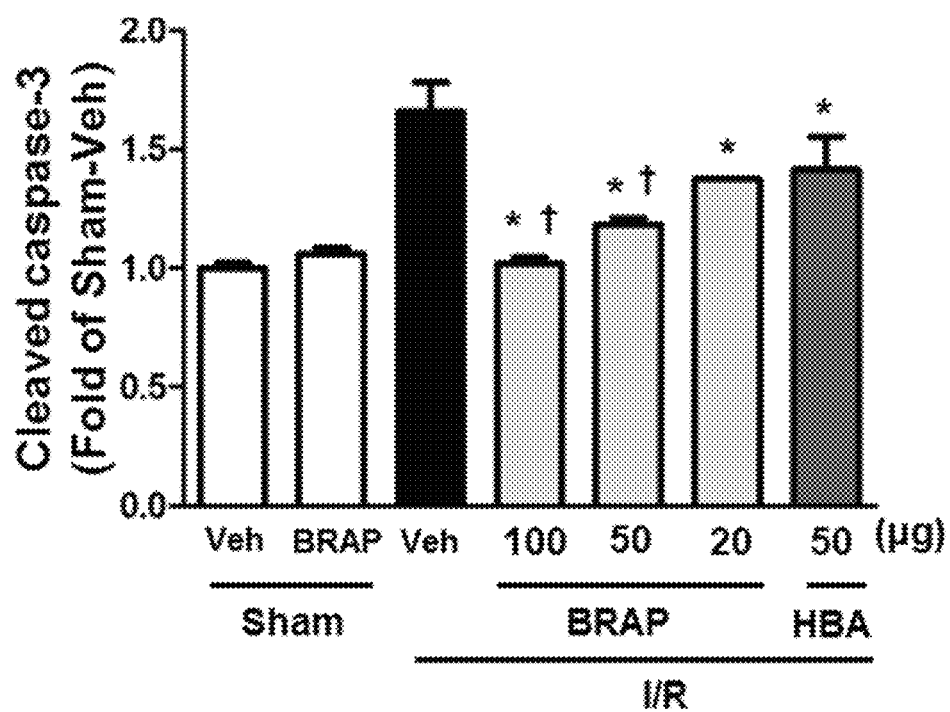
Figure 5D:
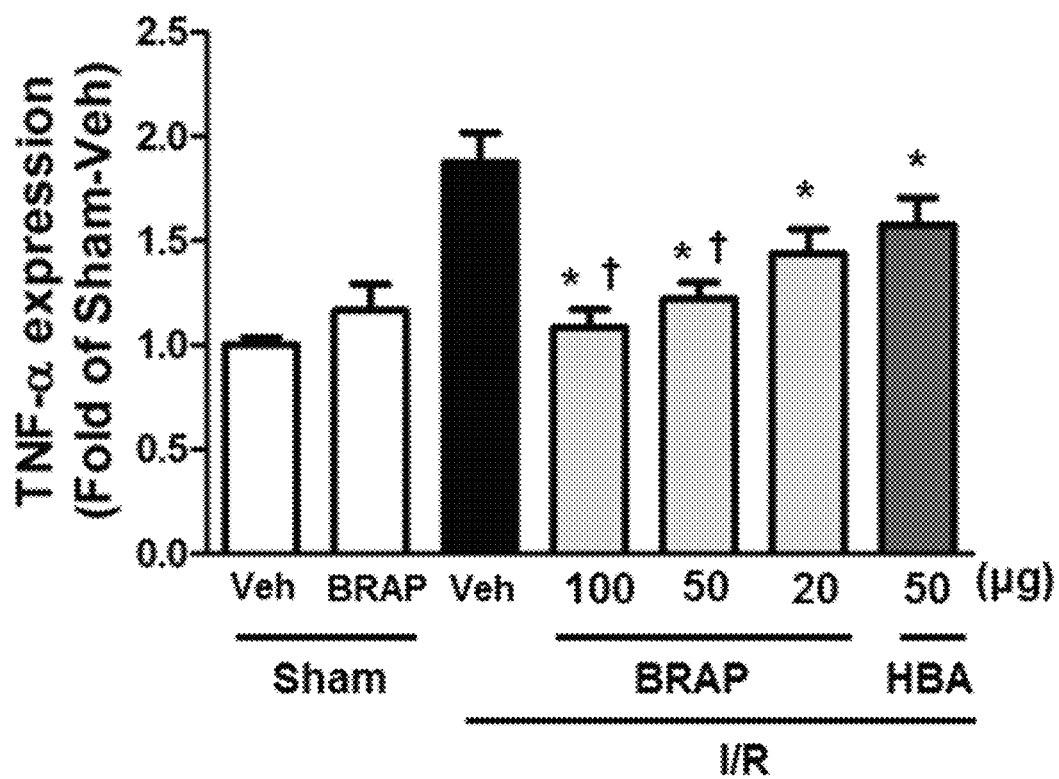

In addition, anti-apoptotic and anti-inflammatory properties of BRAP were also evaluated by measuring the level of cleaved caspase-3 and TNF-α protein expression, respectively. HBA had minimal inhibitory effects on cleaved caspase-3 and TNF-α. On the other hand, the same dose of BRAP showed significant inhibition of caspase-3 and TNF-α activities (FIGS. 5C-5D). These results demonstrate the anti-inflammatory and anti-apoptotic properties of BRAP in a mouse model of hepatic I/R injury in vivo.

Figure 24:
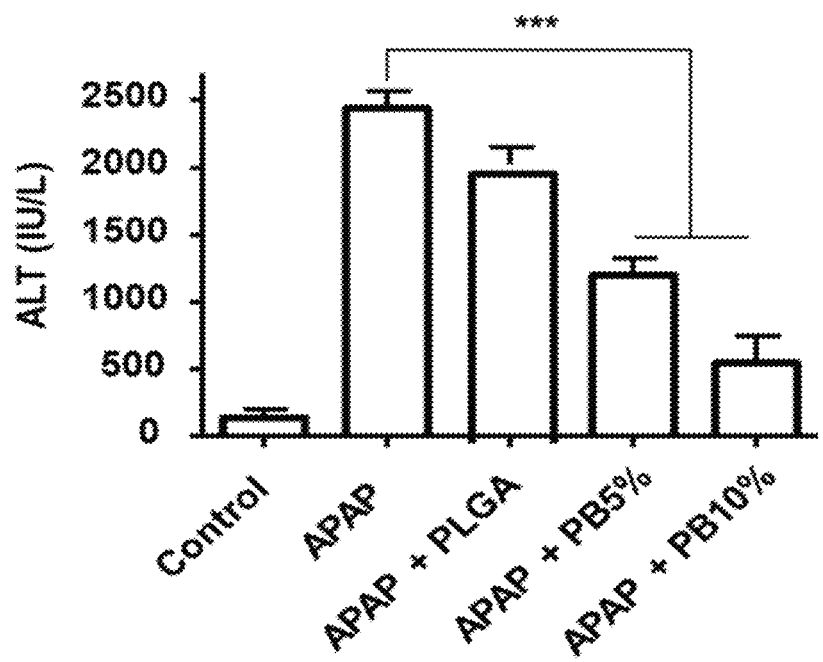
FIG. 24 is a bar graph illustrating the therapeutic activity of BRAP-encapsulated PLGA microparticles in acetaminophen (APAP)-induced acute liver failure. Acute liver failure was induced in mice (8 weeks old) by intraperitoneal injection of APAP. PLGA or BRAP-encapsulated PLGA microparticles were injected intravenously into each animal at a dose of 5 mg/kg. The level of alanine transaminase (ALT) in plasma was determined at 24 hours post-treatment as described infra. Values shown are mean±s.d. (n=4). ***P<0.001.

Furthermore, in an animal model of acute liver failure, BRAP-encapsulated PLGA microparticles demonstrated therapeutic activity in mice with acetaminophen (APAP)-induced acute liver failure, as evidenced by a reduction in the amount of ALT detected in plasma following treatment of the animals with the microparticles (FIG. 24).

Example 7: Effects of BRAP in a Cardiac I/R Injury Model

Figure 6A:
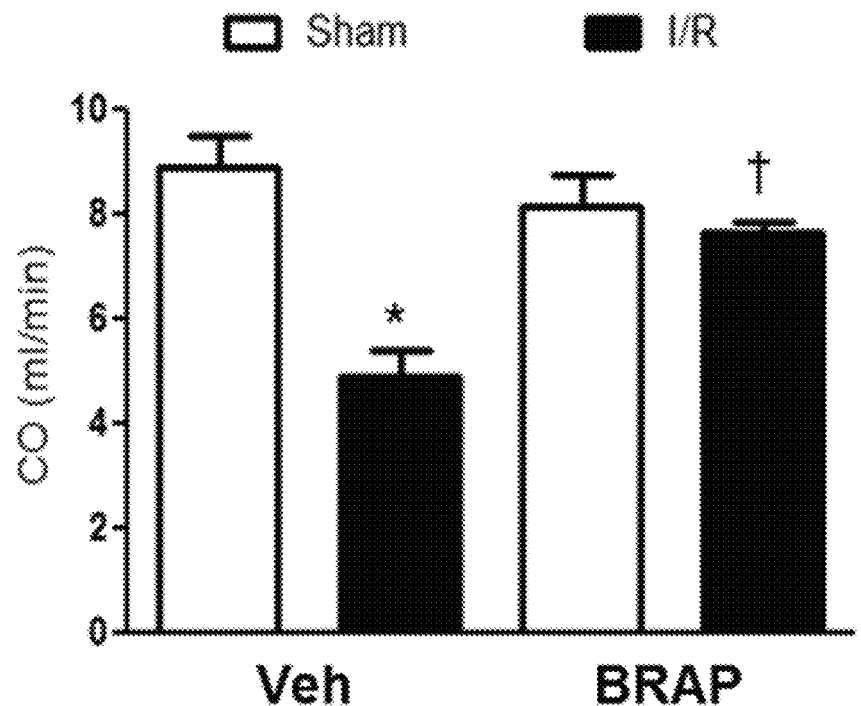
FIGS. 6A-6F, is a set of images and bar graphs illustrating effects of BRAP on cardiac function after I/R.
Figure 10A:
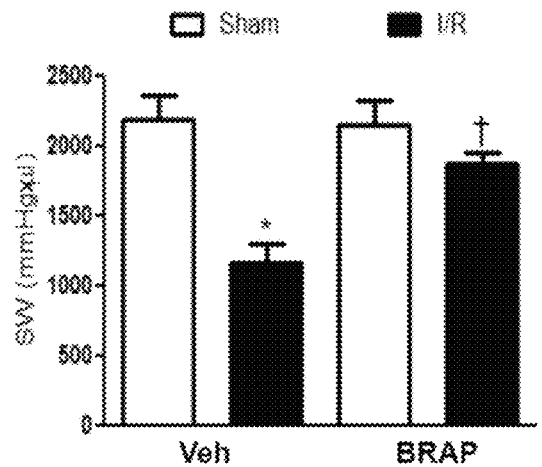
FIGS. 10A-10C, is a series of bar graphs illustrating the Stroke wok (SW) (FIG. 10A), ejection fraction (EF) (FIG. 10B), and fractional shortening (FS) (FIG. 10C) with BRAP treatment after I/R injury. *$p<0.05$ versus sham of each group, †$p<0.05$ versus Veh I/R (n=4-6/group).
Figure 10B:
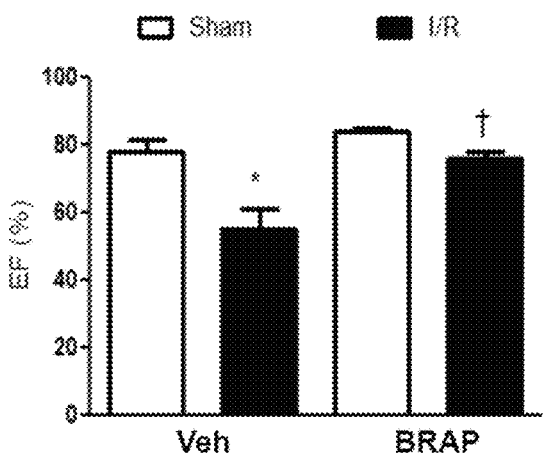
Figure 10C:
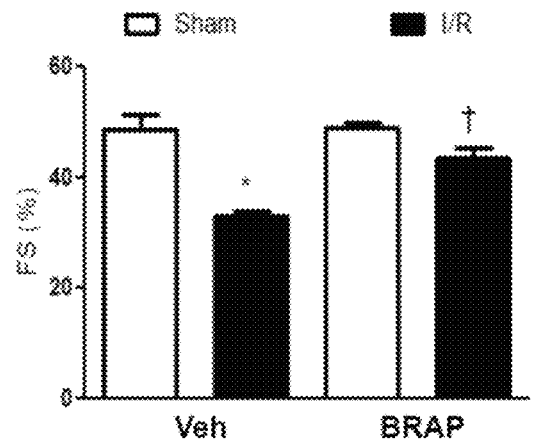

The beneficial effects of BRAP were further investigated using a mouse model of cardiac I/R injury in vivo. After 45 minutes of ischemia, BRAP (1.5 mg/kg) or vehicle was administered i.p. at the time of reperfusion, and then daily (1.5 mg/kg/day) for 2 weeks. For cardiac functional analysis, pressure-volume (PV) loop measurement and echocardiography were performed at 2 weeks after I/R surgery. PV loop analysis showed a significant reduction of cardiac output (CO), stroke work (SW) and ejection fraction (EF) 2 weeks after I/R injury (FIGS. 6A and 10). Additional cardiac functional analysis using echocardiography also showed significant decrease in fractional shortening (FS) at 2 weeks after I/R surgery (FIG. 10C). Administration of BRAP significantly attenuated I/R-induced cardiac dysfunction both by PV loop analysis and echocardiography.

Figure 6B:
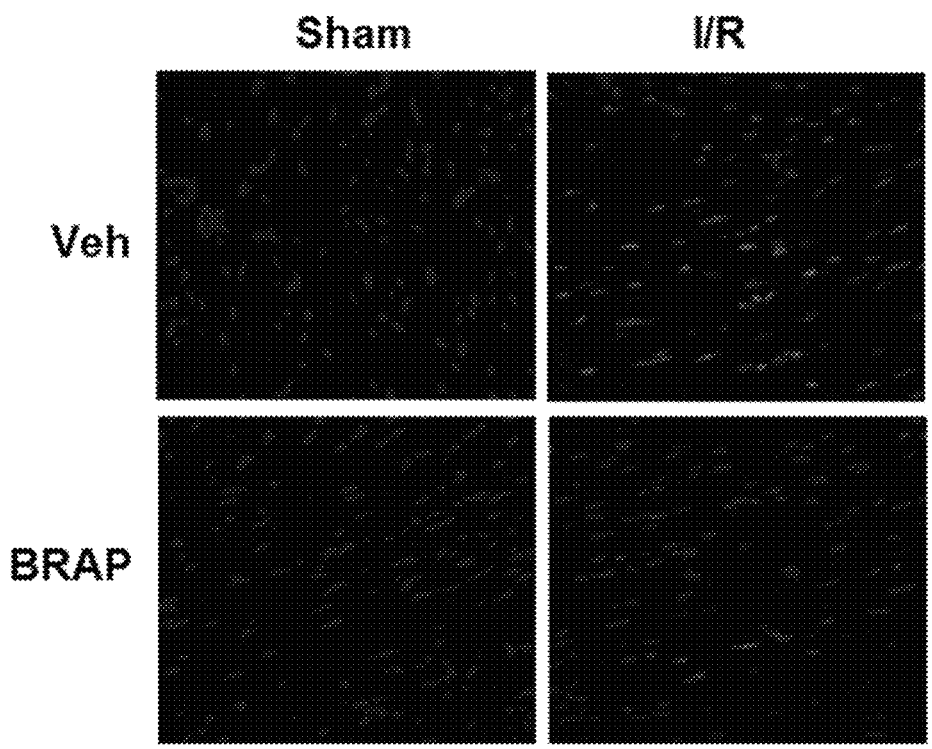
Figure 6C:
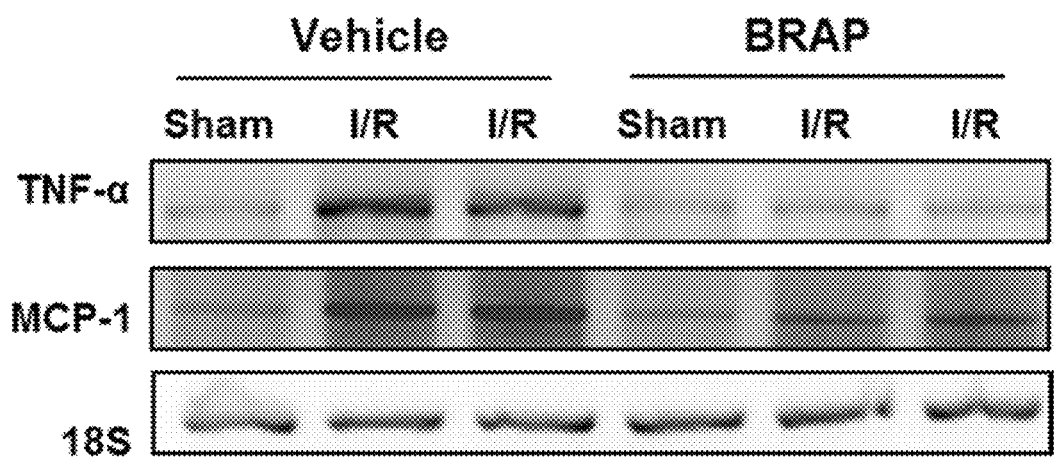
Figure 11A:
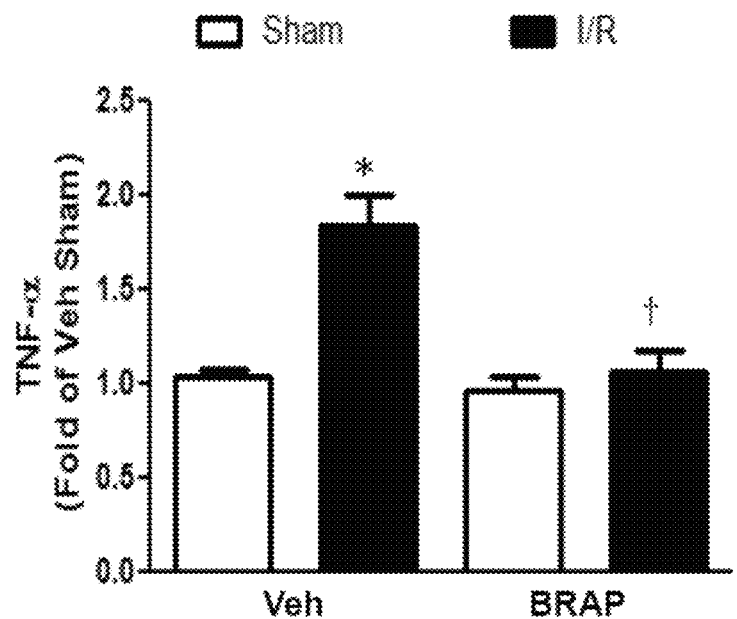
FIGS. 11A-11B, is a series of bar graphs illustrating quantitative analysis of mRNA expression of TNF-α (FIG. 11A) and MCP-1 (FIG. 11B) with BRAP treatment after I/R injury. *$p<0.05$ versus sham of each group, †$p<0.05$ versus Veh I/R (n=4-6/group).
Figure 11B:
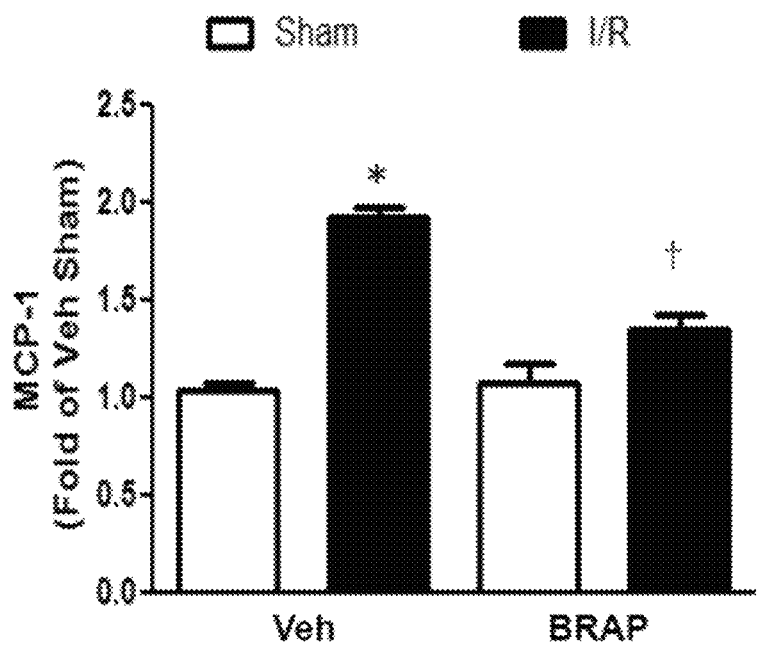

Studies were then performed to determine whether the benefits of BRAP after I/R were associated with attenuation of oxidative stress, inflammation, and apoptosis. These mechanistic analyses were performed in heart tissues 24 hours after cardiac I/R injury. To explore anti-oxidant effects of BRAP by scavenging ROS, dihydroethidium (DHE) staining was used as indicator of ROS generation after I/R. The generation of ROS was significantly increased after I/R in vehicle-treated mice (FIG. 6B). BRAP administration significantly decreased DHE staining, demonstrating the scavenging effect of BRAP on ROS generation after I/R. In addition, evaluation of inflammatory responses showed that I/R injury significantly increased mRNA levels of TNF-α and monocyte chemotactic protein-1 (MCP-1) (FIGS. 6C, 11A and 11B). BRAP administration decreased TNF-α and MCP-1 expressions compared with vehicle-treated mice.

Figure 6D:
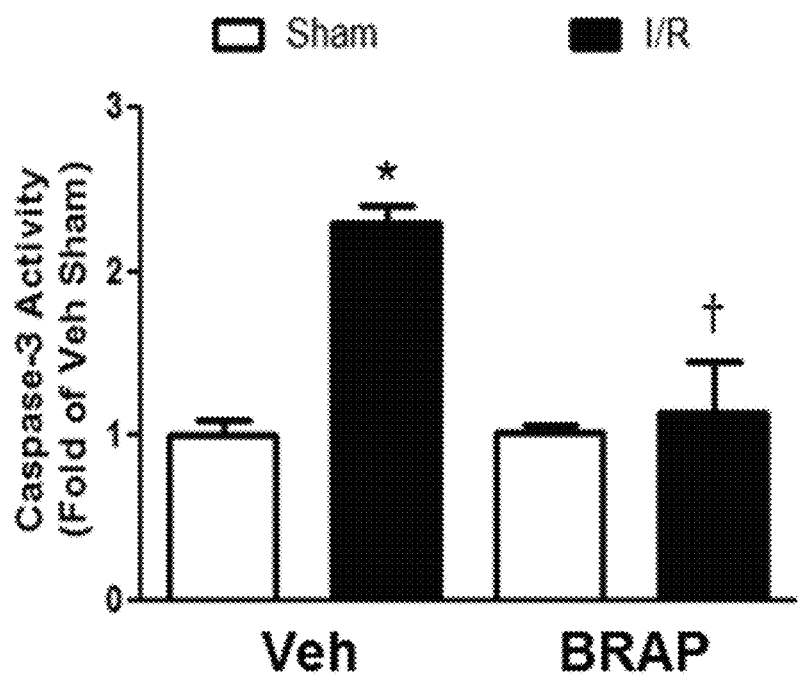
Figure 6E:
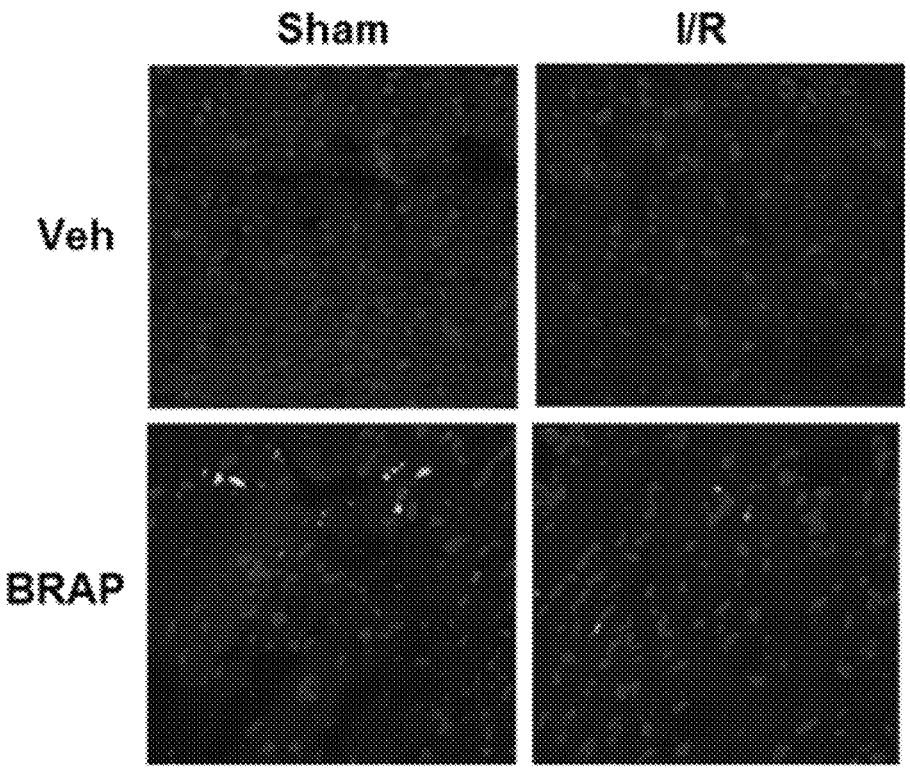
Figure 6F:
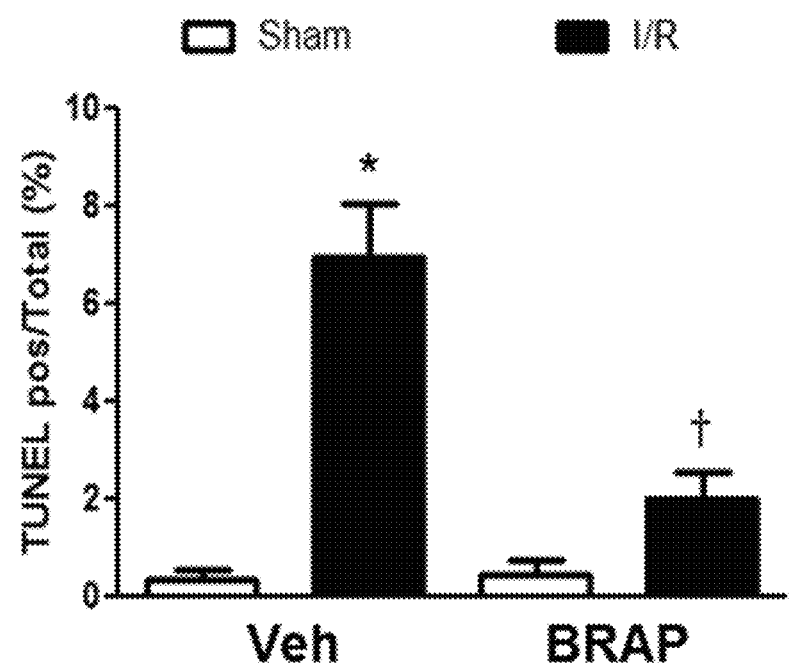

To assess the anti-apoptotic effect of BRAP after I/R, caspase-3 activity assay and TUNEL staining were performed. Caspase-3 activity, a marker of apoptosis, was significantly increased after I/R (FIG. 6D). BRAP effectively reduced caspase-3 activation. In addition, I/R increased cardiomyocyte apoptosis as demonstrated by significant increase in TUNEL-positive cardiomyocytes after 24 hours of I/R (FIGS. 6E-6F), which was effectively inhibited by BRAP. These results demonstrated that BRAP treatment effectively prevented I/R-induced cardiac damage by blocking oxidative stress and inflammation, resulting in inhibition of apoptosis.

Example 8: Toxic Effects of BRAP

Figure 7A:
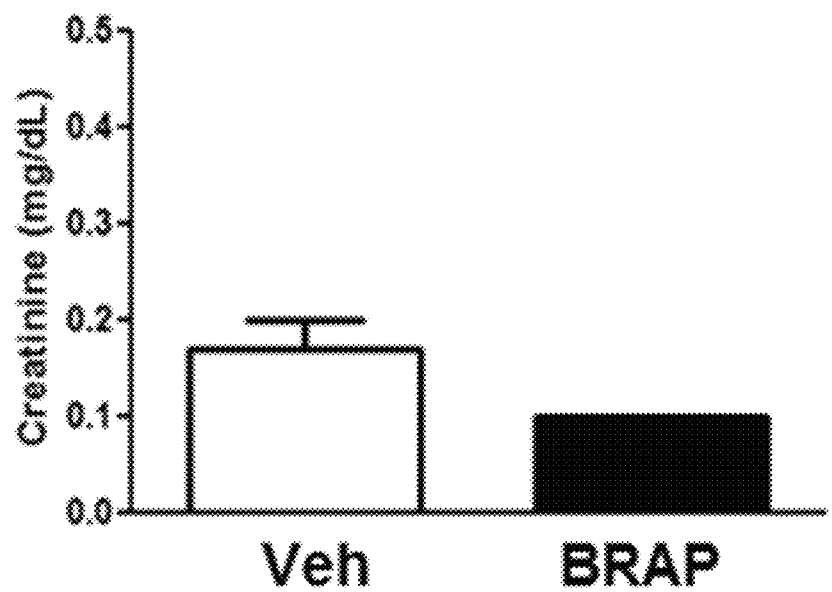
FIGS. 7A-7C, is a set of images and bar graphs illustrating the safety profile of BRAP (1.5 mg/kg/day) after daily intraperitoneal administration for 7 days.
Figure 7B:
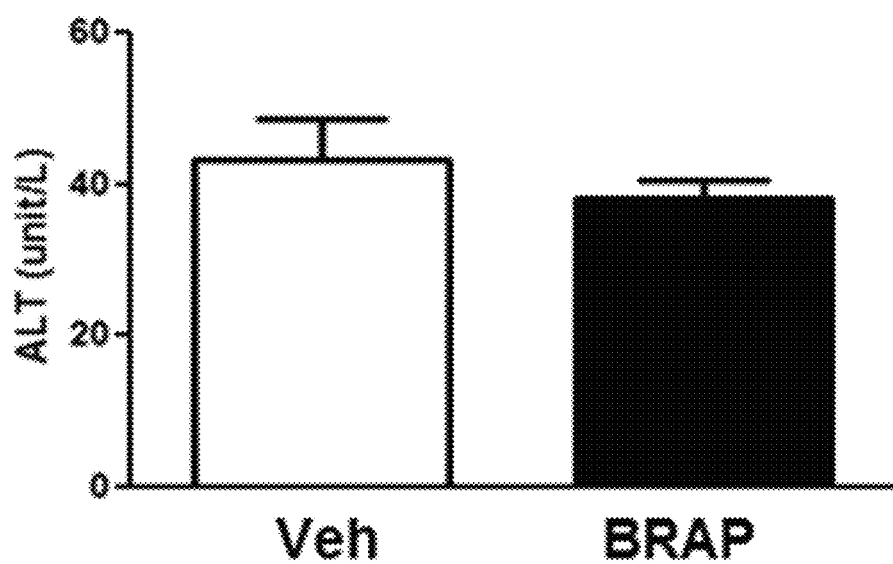
Figure 7C:
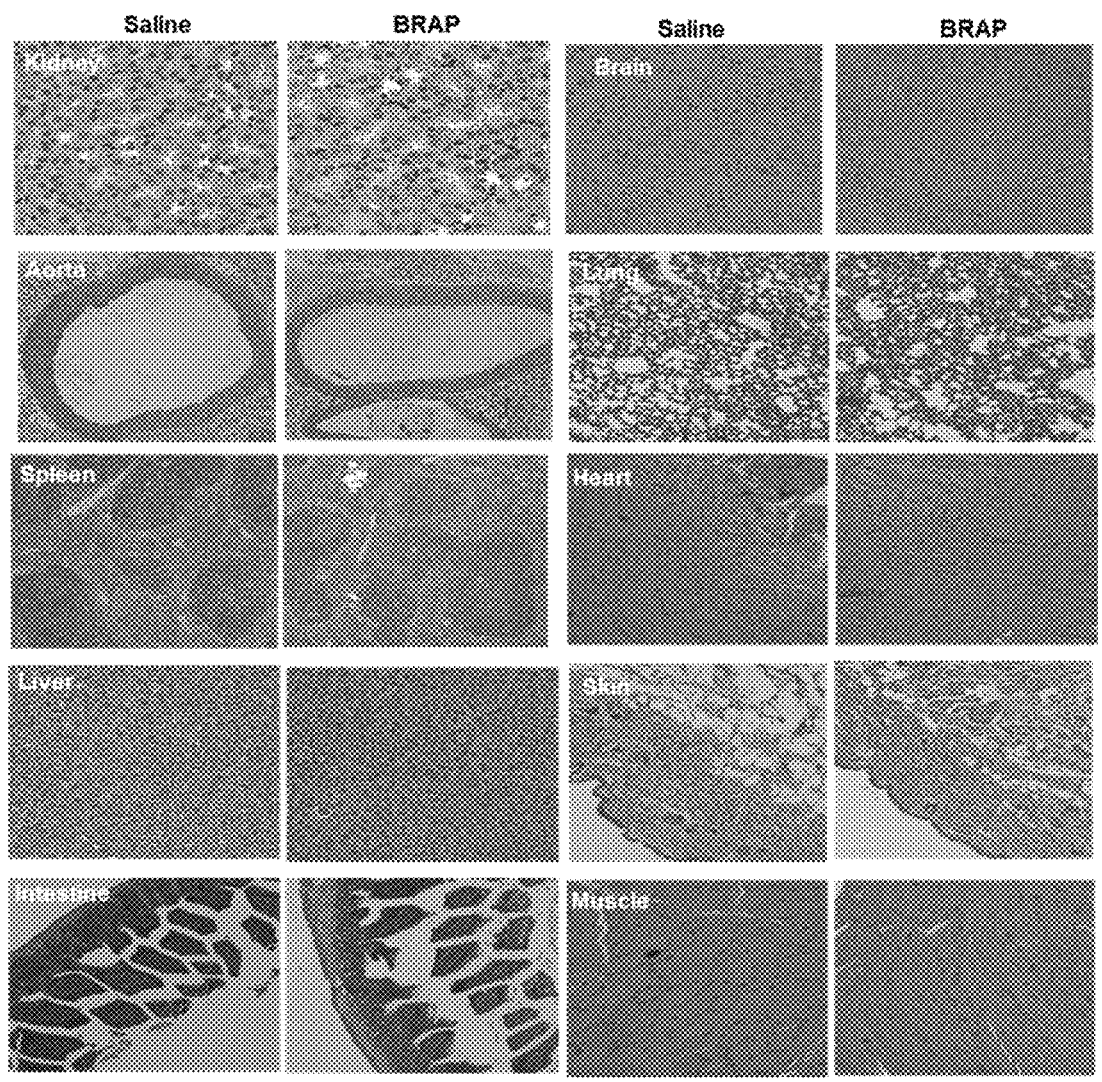
Figure 8A:
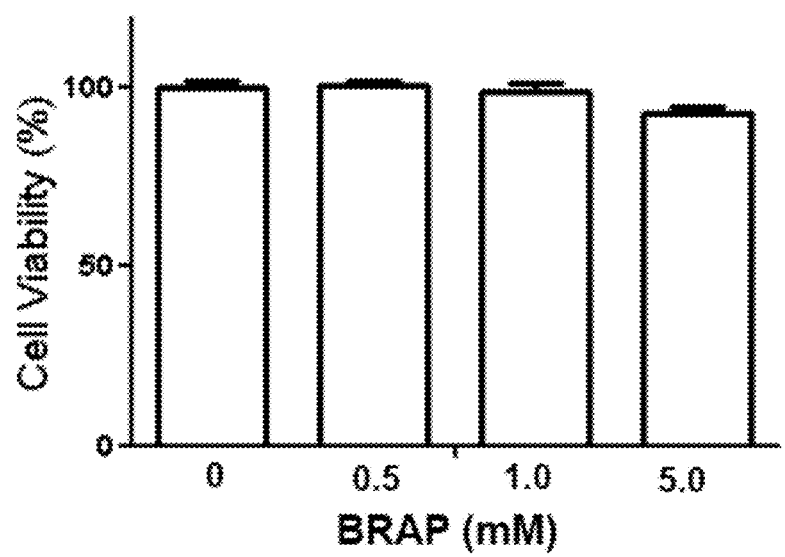
FIGS. 8A-8B, is a set of bar graphs illustrating biocompatibility profiles of BRAP assessed by MTT assay in human embryonic kidney (HEK 293) cells (FIG. 8A) and mouse embryonic fibroblast (NIH 3T3) cells (FIG. 8B).
Figure 8B:
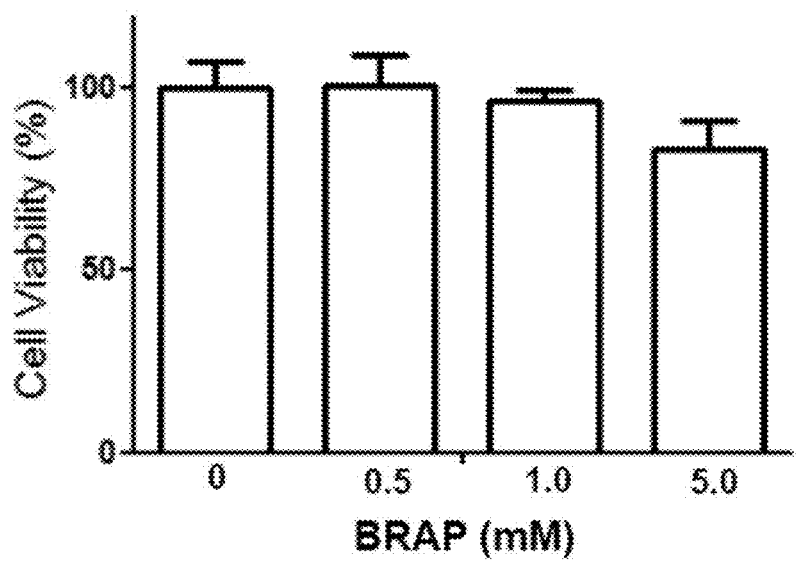

To determine the potential cumulative toxic effects of BRAP, BRAP (1.5 mg/kg/day) was administered daily for 7 days in mice. Serum tests for renal and hepatic functions showed no significant abnormalities after 7 days (FIGS. 7A-7B). In addition, there was no significant histological evidence of accumulated toxicity in the different organs after

Figure 12:
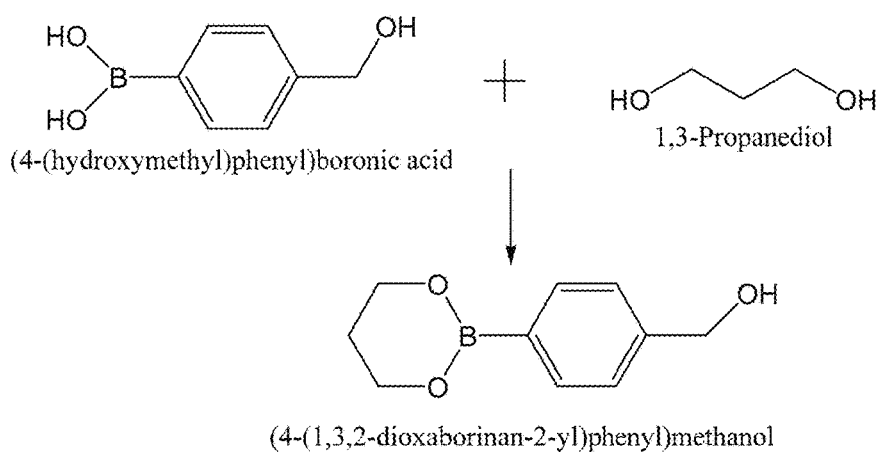
FIG. 12 illustrates the synthesis and $^1H$ NMR spectrum of 4-(1,3,2-dioxaborinan-2-yl)phenyl methanol.
Figure 12:
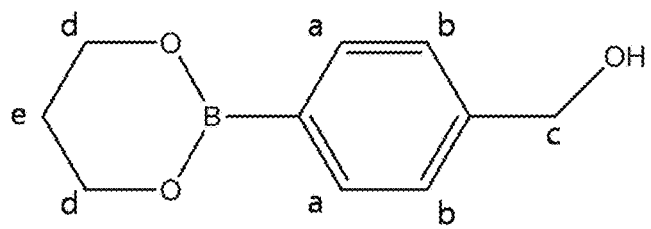
Figure 12:
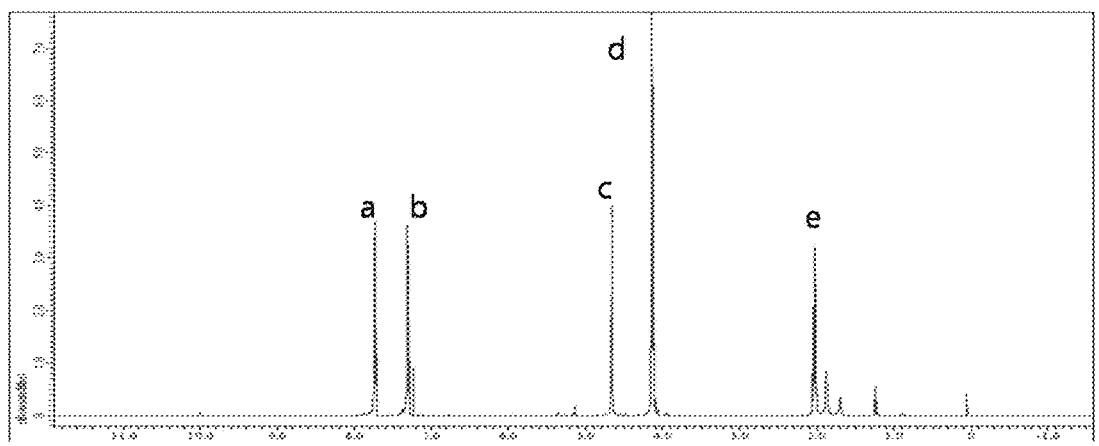

Example 9: Synthesis of 4-(1,3,2-Dioxaborinan-2-yl)phenyl)methanol (4-Hydroxymethyl)phenyl)boronic acid was added to THF, forming a suspension. 1,3-Propanediol was added and the suspension was stirred for 24 hours. After 24 hours, the mixture became clear. Sodium sulfate was then added and the mixture was stirred for 24 hours further. After filtration, the product was isolated from solution using a rotary evaporator. the crude product was purified by column chromatography (ethylacetate:hexane=2:3) (See FIG. 12).

Figure 13:
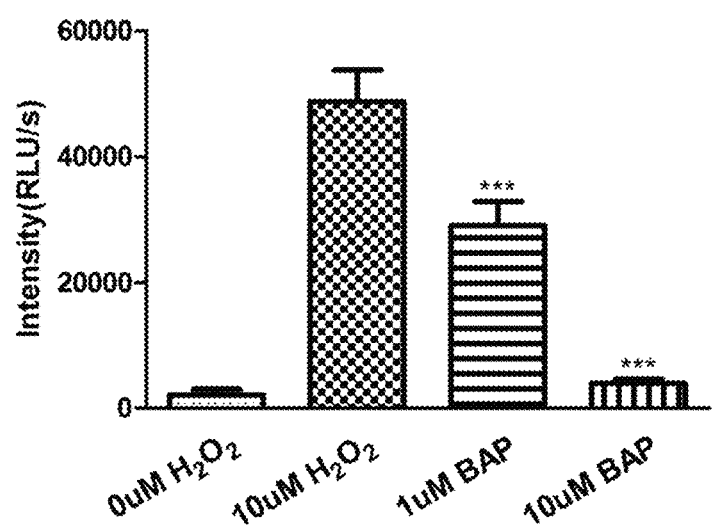
FIG. 13 is a bar graph illustrating $H_2O_2$ scavenging by 4-(1,3,2-dioxaborinan-2-yl)phenyl methanol. In the experiment, the chemiluminescence intensity was measured after the reaction with diphenyl oxalate solution including rubrene. The boronate (1 μM, or 10 μM) was added in the $H_2O_2$ solution (10 μM). After 1 min reaction with $H_2O_2$, diphenyl oxalate solution was added to the $H_2O_2$ solution, and the chemiluminescence intensity was measured by using a luminometer (Femtomaster FB 12, Zylux Corporation, TN, US).

Example 10: $H_2O_2$ Scavenging by 4-(1,3,2-Dioxaborinan-2-yl)phenyl)methanol The ability of the boronate compound to scavenge $H_2O_2$ was evaluated by measuring the chemiluminescence intensity after the reaction with diphenyl oxalate solution including rubrene. The boronate (1 µM, or 10 µM) was added in the $H_2O_2$ solution (10 µM). After 1 min reaction with $H_2O_2$, diphenyl oxalate solution was added to the $H_2O_2$ solution, and the chemiluminescence intensity was measured by using a luminometer (Femtomaster FB 12, Zylux Corporation, TN, US; FIG. 13). Similar scavenging of $H_2O_2$ was exhibited by BRAF-encapsulated PLGA microparticles (FIG. 21).

The results described herein above were carried out using the following materials and methods.

Synthesis of BRAP 4-(Hydroxymethyl)phenylboronic acid and 2-(hydroxymethyl)-2-methylpropane-1,3-diol were dissolved in dry tetrahydrofuran and the mixture was allowed for at room temperature with mechanical stirring. When the reaction mixture became clear after 24 hours of reaction, $Na_2SO_4$ was added. The reaction was allowed at room temperature overnight and the solvent was evaporated. BRAP was obtained using silica gel chromatography (hexane/ethyl acetate=70/30).

Hydrolytic Kinetic of BRAP

BRAP was dissolved in PBS (pH 7.4) at a concentration of 1 mM and was incubated at 37° C. in the presence of 100 µM of $H_2O_2$. The concentration of HBA generated from BRAP was measured using a UV spectrometer at appropriate time points.

Cytotoxicity and $H_2O_2$ Scavenging of BRAP 3-(4,5-Dimethylthiazil-2yl)-2,5-diphenyltetrazolium bromide (MTT) assay was performed to evaluate the cytotoxicity of BRAP. NIH 3T3 cells were cultured at a density of $1\times10^5$ cells/well in a 24 well plate, and RAW 264.7 cells and HEK cells were also cultured at a density of $2\times10^5$ cells/well in a 24 well plate. Cells were incubated for 24 hours to reach ~80% confluency. Cells were treated with various amount of BRAP and incubated for 24 hours. Each well was given 100 µL of MTT solution and was incubated for 4 h. 200 µL of dimethyl sulfoxide (DMSO) were added to each well to dissolve the resulting formazan crystals. After 10 min incubation, the absorbance at 570 nm was measured using a microplate reader (Biotek Instruments, Winooski, Vt.). The cell viability was determined by comparing the absorbance of BRAP treated cells that of control cells.

The ability of BRAP to scavenge $H_2O_2$ was evaluated by measuring the chemiluminescence intensity after the reaction with diphenyl oxalate solution including rubrene. BRAP (1 µM, 5 µM, 10 µM, 20 µM) was added in the $H_2O_2$ solution (10 µM). After 1, 5 or 10 min reaction with $H_2O_2$, diphenyl oxalate solution was added to the $H_2O_2$ solution, and the chemiluminescence intensity was measured by using a luminometer (Femtomaster FB 12, Zylux Corporation, TN, US).

Confocal Laser Scanning Microscopy

Cells were pretreated with 250 µM of $H_2O_2$ for 24 hours and then treated with HBA or BRAP for 15 min. To measure the level of intracellular ROS, cells were treated with DCFH-DA for 15 min. Cells were washed with fresh medium twice and analyzed using a confocal scanning microscope.

Animal Surgeries

Hepatic I/R surgery was performed in 12 week-old male mice. Briefly, mice were anaesthetized, and midline incision was performed for laparotomy. After identifying the portal triad and biliary tree, the main trunk of hepatic artery and portal vein were clamped with vascular clip except for the vasculatures to the right lower lobe to achieve ischemic injury to approximately 70% of the liver. After 1 hour of ischemia, reperfusion was achieved by releasing the vascular clip. No vascular clamp was done for the sham group of mice.

Cardiac I/R surgery was performed in 12 week-old male mice as described in Choudhury, et al., 2011, Basic Res Cardiol 106:397. Briefly, mice were anaesthetized and placed on a rodent ventilator (model 687, Harvard Respirator). After thoracotomy, the left anterior descending artery (LAD) artery was identified and ligated with a 7-0 silk suture tied around a specialized 30 G-catheter. The animal remained under anesthesia and ventilation for 45 min of ischemia, after which reperfusion was achieved by cutting the suture and re-establishing arterial perfusion. Sham operated mice underwent the same procedure without LAD occlusion.

Cardiac Functional Analysis

Cardiac function was evaluated using the pressure-volume loop measurement and echocardiography 2 weeks after I/R as described in Lee, et al., 2013, Sci Rep 3:2233. Pressure-volume parameters were measured after isoflurane (2%) inhalant anesthesia using a 1.4 Fr. micro-tip pressure-volume catheter (Scisense Inc, Ontario, Canada) inserted into the right common carotid artery. The catheter was gently advanced into the left ventricle to obtain LV hemodynamic parameters. Data was recorded using a Powerlab system (ADInstruments, Colorado Springs, Colo.). Beat by beat pressure-volume parameters including heart rate (HR), stroke volume (SV), stroke work (SW) and cardiac output (CO) were measured and analyzed using CardioSoft Pro software (CardioSoft, Houston, Tex.). Transthoracic echocardiography was performed using a Vevo2100 ultra-high frequency small animal imaging system with MS400 transducer (18-38 MHz) (Visualsonics, Toronto, Canada).

Apoptosis Assays

For liver apoptosis assay, terminal deoxynucleotidyl transferase dUTP nick end labeling (TUNEL) staining was performed using a DeadEnd™ Fluorometric TUNEL kit (Promega, Madison, Wis.). Tissue sections were stained for nuclei (4',6-diamidino-2-phenylindole (DAPI) staining) and apoptotic nuclei (TUNEL staining) and analyzed using a confocal laser scanning microscope. For heart tissues, TUNEL staining was performed using in situ cell death detection Kit, fluorescein (Roche Applied Science, Indianapolis, Ind.). To distinguish cardiomyocyte from non-cardiomyocyte nuclei, triple stain for nuclei (DAPI staining), apoptotic nuclei (TUNEL staining), and cardiomyocytes (α-Actinin staining) was used, and the stained sections were analyzed using confocal microscopy. A minimum of ~10 high power fields with ~2000 nuclei/field were counted for each sample.

Caspase-3 and PARP Activity Assay

The activity of caspase-3 was determined with colorimetric assay kit (R&D Systems, Minneapolis, Minn.) as described in Choudhury, et al., 2011, Basic Res Cardiol 106:397; Bae, et al., 2010, Am J Physiol Heart Circ Physiol 299:H1374. Briefly, protein samples were added to substrates of Acetyl-Asp-Glu-Val-Asp-p-nitroanilide. The enzyme-catalyzed release of p-nitroanilide was measured at 405 nm. For PARP activity assay, activity was measured at 450 nm by incorporation of biotinylated poly (ADP-ribose) onto histone-coated proteins in plate using colorimetric assay kit (R&D Systems, Minneapolis, Minn., USA).

Reverse Transcriptase-Polymerase Chain Reaction (RT-PCR) and Western Blot Analysis Heart tissues were collected for molecular analyses were performed in Bae, et al., 2010, Am J Physiol Heart Circ Physiol 299:H1374. For RT-PCR ribosomal 18S primers acted as internal controls and all RT-PCR signals were normalized to the 18S signal of the corresponding RT products. For Western blot analysis, the protein content was measured using BCA assay. Actin protein expression was used as an internal control for protein loading.

Reactive Oxygen Species (ROS) Staining

The optimal cutting temperature (OCT)-embedded tissues were fixed in 4% paraformaldehyde. Tissue sections were incubated with 5 µM dihydroethidium (DHE, Sigma-Aldrich) at 37° C. for 30 min in a humidified chamber protected from light. Then, 4',6-diamidino-2-phenylindole (DAPI) was applied. Images were acquired by confocal fluorescence microscope.

Statistical Analyses

Data were expressed as means±SEM. Comparisons between and within groups were conducted with unpaired Student t-tests and repeated-measures ANOVA using GraphPad Prism 5.0 (San Diego, Calif.), respectively. Probability (p) values of <0.05 were considered significant.

Example 11: Effect of Oral Administration of BRAP Against Renal Ischemia/Reperfusion (I/R) Injury BRAP administered orally was tested in a kidney I/R injury model in the mouse. In this model, one of the mouse's kidney was subjected to ischemia for about 30 min, using a combination of unilateral clamping and contralateral nephrectomy. BRAP was administered orally to the mice at two time points: the night before the surgery, and immediately before the I/R surgery. The read-out markers after I/R comprised: creatinine levels 24 hours after reperfusion; tumor necrosis factor alpha (TNF-α) and monocyte chemoattractant protein-1 (MCP-1) (both inflammatory markers); DHE staining (monitoring for ROS generation); and TUNEL staining (monitoring for apoptosis).

Figure 14:
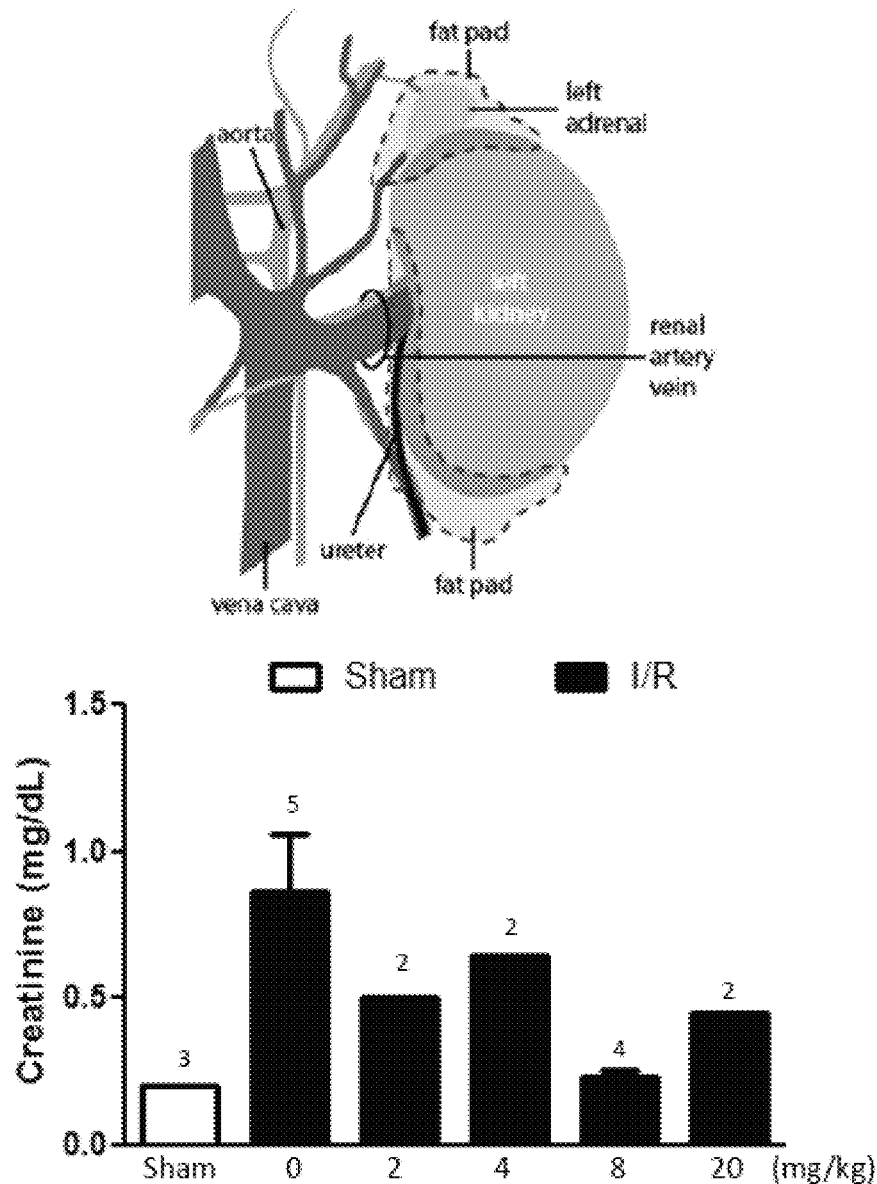
FIG. 14 comprises (on top) a representation of a kidney and (on bottom) a bar graph that illustrates creatinine levels 24 hours after reperfusion for various oral doses of BRAP. The number of animals assayed for each dose are listed on top of each bar.
Figure 15:
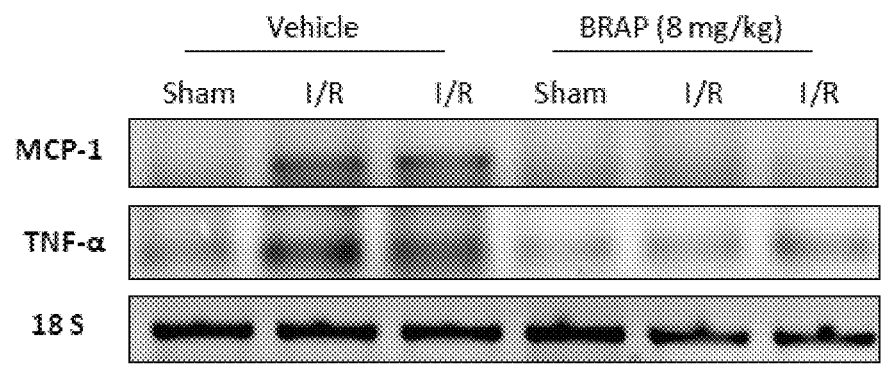
FIG. 15 is a series of images that illustrate inflammation markers TNF-α and MCP-1 24 hours after reperfusion.
Figure 16:
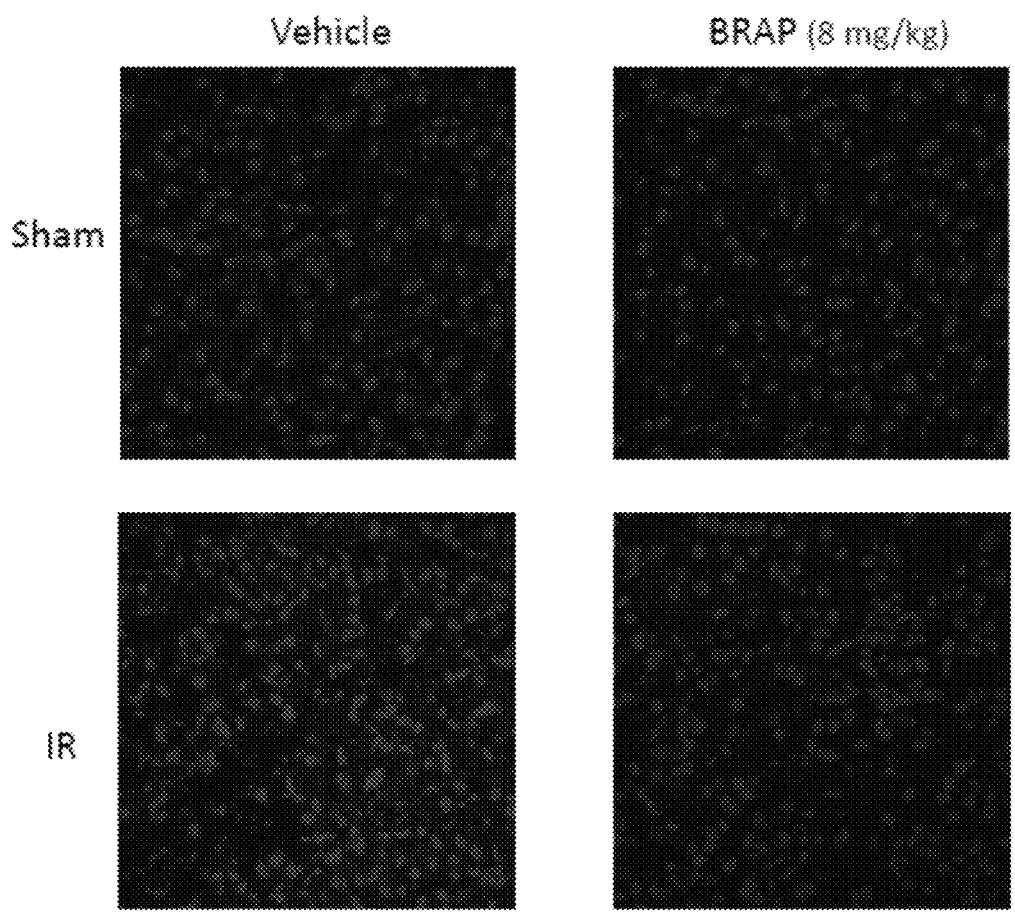
FIG. 16 is a series of images that illustrate DHE staining after I/R. DHE staining is shown in red, and DAPI is shown in blue.
Figure 17:
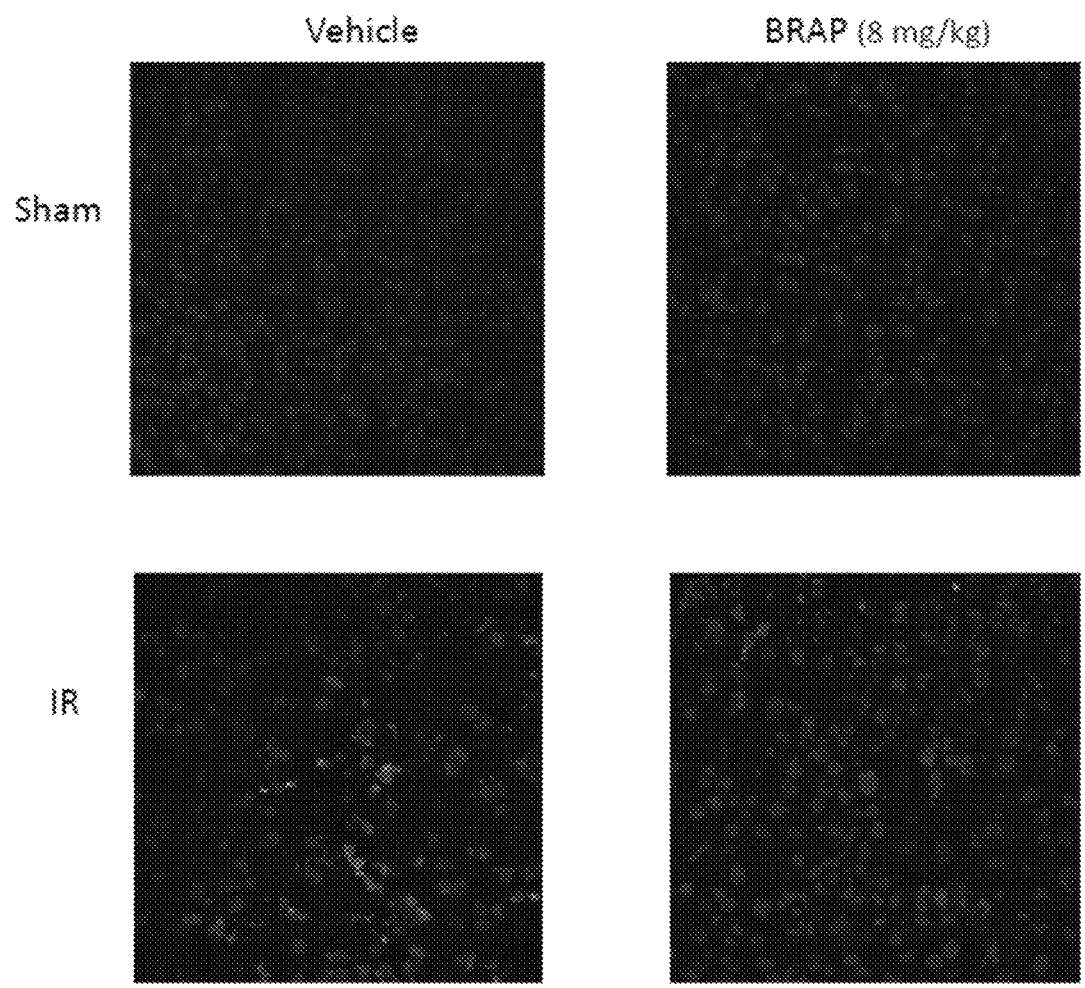
FIG. 17 is a series of images that illustrate TUNEL staining after I/R. TUNEL is shown in green, and DAPI is shown in blue.

The results indicated that daily oral administration of BRAP (8 mg/kg) resulted in significant improvement in renal function in the model of kidney I/R injury after 4 days (FIG. 14). Further, as demonstrated herein, activation of inflammatory markers, TNF-α and MCP-1, was significantly attenuated with oral administration of BRAP (FIG. 15). DHE staining (FIG. 16), which is a marker for ROS generation, and TUNEL staining (FIG. 17), which is a marker for apoptosis, were also significantly reduced upon oral administration of BRAP.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of reducing inflammation associated with ischemic reperfusion injury in a subject, the method comprising administering to the subject an effective amount of a microparticle comprising 4-(hydroxymethyl)phenylboronic ester, wherein the boronic ester comprises an alcohol selected from the group consisting of a diol, triol, tetraol, pentaol, hexaol and a higher polyol, wherein the alcohol and 4-(hydroxymethyl)phenylboronic acid are covalently conjugated to form the boronic ester, wherein the microparticle comprises a polymer or liposome, thereby reducing inflammation associated with ischemic reperfusion injury relative to a reference.

2. The method of claim 1, wherein the method reduces TNF-α and/or inducible nitric oxide synthase levels in the subject.

3. The method of claim 1, wherein the ester is encapsulated in a poly(lactic-co-glycolic acid) (PLGA) microparticle.

4. The method of claim 1, wherein the alcohol comprises 1,3-propanediol or 2-(hydroxymethyl)-2-methylpropane-1,3-diol.

5. The method of claim 1, wherein the boronic ester comprises 4-(5-(hydroxymethyl)-5-methyl-1,3,2-dioxaborinan-2-yl)phenyl methanol or 4-(1,3,2-dioxaborinan-2-yl) phenyl methanol.

6. The method of claim 1, wherein the polymer comprises at least one selected from the group consisting of poly(lactic acid) (PLA), poly(glycolic acid) (PGA), poly(lactic-co-glycolic acid) (PLGA), and poly(ε-caprolactone) (PCL).

7. The method of claim 1, wherein the reference is the level of inflammation present in an untreated control subject.

8. The method of claim 1, wherein the inflammation is associated with acute coronary syndrome, hepatic ischemia, renal ischemia, brain ischemic injury, coronary artery disease, cardiopulmonary bypass surgery and/or a vascular thromboembolic event.

* * * * *